United States Patent
Sato

(10) Patent No.: US 8,657,749 B2
(45) Date of Patent: Feb. 25, 2014

(54) ULTRASONIC PUNCTURE NEEDLE

(71) Applicant: Olympus Medical Systems Corp., Tokyo (JP)

(72) Inventor: Masatoshi Sato, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/685,224

(22) Filed: Nov. 26, 2012

(65) Prior Publication Data

US 2013/0144164 A1 Jun. 6, 2013

Related U.S. Application Data

(63) Continuation of application No. PCT/JP2012/063382, filed on May 24, 2012.

(60) Provisional application No. 61/490,676, filed on May 27, 2011.

(51) Int. Cl.
*A61B 8/00* (2006.01)

(52) U.S. Cl.
USPC ........... 600/439; 600/407; 600/437; 600/441; 600/443; 600/104

(58) Field of Classification Search
USPC .......... 600/437, 441, 443, 447, 160, 104, 439
See application file for complete search history.

(56) References Cited

FOREIGN PATENT DOCUMENTS

| JP | A-11-332867 | 12/1999 |
|----|-------------|---------|
| JP | A-2000-139926 | 5/2000 |
| JP | A-2002-306497 | 10/2002 |
| JP | A-2002-306606 | 10/2002 |
| JP | A-2007-236684 | 9/2007 |

OTHER PUBLICATIONS

Jan. 29, 2013 Japanese Office Action issued in Japanese Application No. 2012-553525 (with translation).
Jul. 17, 2012 International Search Report issued in Application No. PCT/JP2012/063382 (with translation).

*Primary Examiner* — Joel Lamprecht
(74) *Attorney, Agent, or Firm* — Oliff PLC

(57) ABSTRACT

An ultrasonic puncture needle used in combination with an ultrasonic endoscope including a distal-end hard part, a bendable part, and an operation part, includes: a sheath inserted into an insertion channel of the ultrasonic endoscope; a needle tube that includes an opening; a releasing mechanism that releases a substance. In a state in which the needle tube is disposed inside the bendable part, a periphery of the needle tube receives a force from an inner wall of the insertion channel while the bendable part is in a bent state by the operation part. The needle tube is rotated around a long axis of the insertion channel by the force, such that an axis line matching the direction of the opening in the needle tube protruding from the insertion channel becomes substantially parallel with an ultrasonic scanning face of the ultrasonic endoscope.

14 Claims, 24 Drawing Sheets

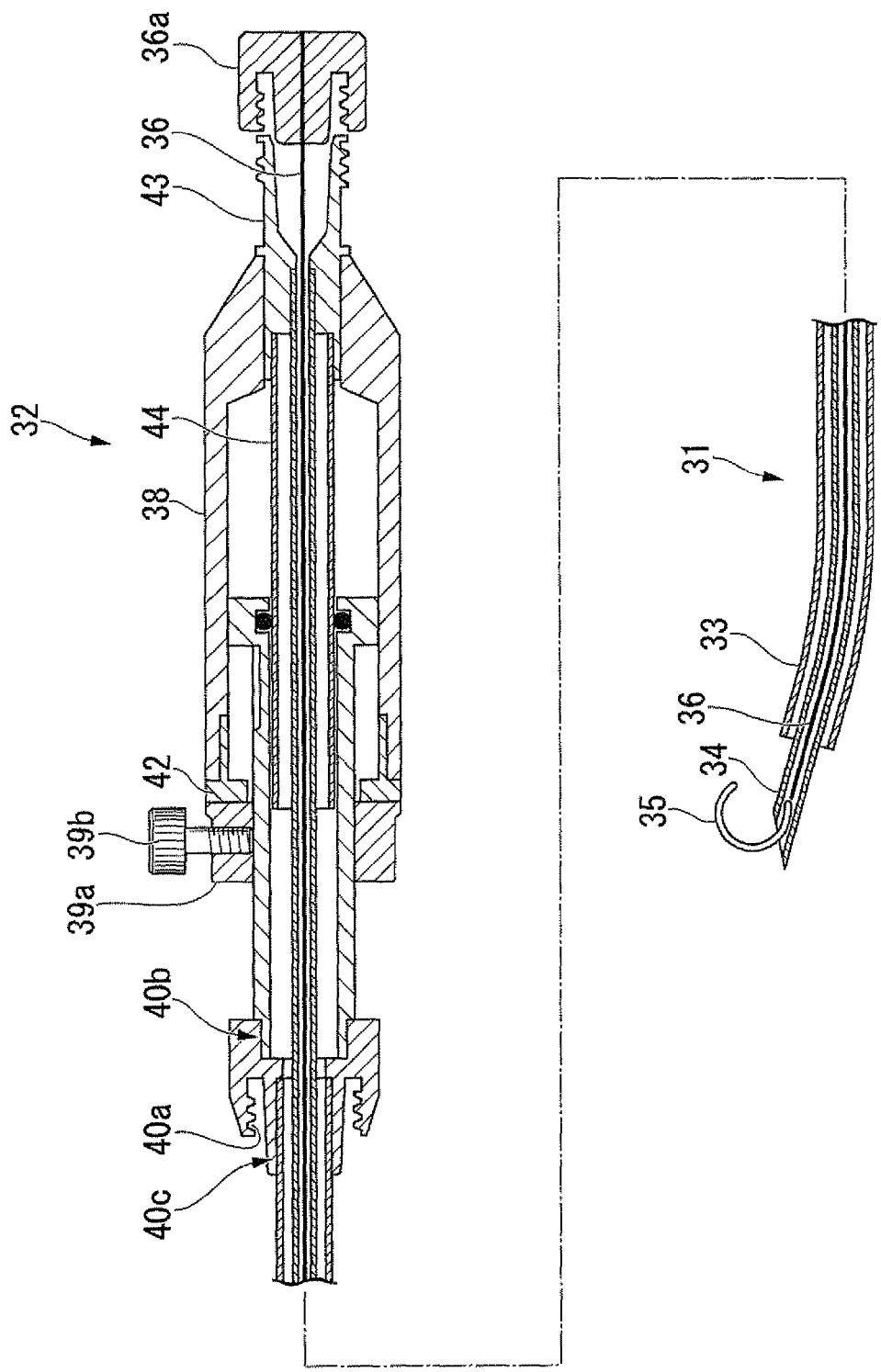

US 8,657,749 B2

ULTRASONIC PUNCTURE NEEDLE

The present application is a continuing application based on PCT Patent Application No. PCT/JP2012/063382, whose priority is claimed on U.S. Provisional Patent Application No. 61/490,676 filed in the US on May 27, 2011. The contents of both the PCT Patent Application and the US Provisional Patent Application are incorporated herein by reference.

BACKGROUND OF THE INVENTION

1. Field of the Invention

The present invention relates to an ultrasonic puncture needle that is inserted into a body cavity and used for delivering medicine and treatment devices into the body.

2. Description of Related Art

Hitherto, to inspect and diagnose an affected part in a body cavity, a procedure of sucking and removing body tissue and body fluid has been performed. This procedure is performed by observing the inside of a body cavity through an ultrasonic endoscope while using a puncture needle to pierce the stomach, the duodenal wall, or the like, and puncture a target region of an underlying organ such as the pancreas, the liver, or the kidney. This is termed Endoscopic Ultrasound-guided Fine-Needle Aspiration (EUS-FNA).

Instead of sucking out tissue or body fluid, the EUS-FNA procedure is recently being applied in research into treatment procedures for delivering medicine, a marker, or a substance such as a radioactive source from a puncture needle directly to the region of interest. In such treatment procedures, by delivering the substance accurately to the region of interest, we can expect the effect of the treatment to be enhanced and side-effects to be reduced. It is therefore preferable to perform the procedure while using an ultrasonic endoscope to observe the substance as it is actually being delivered.

SUMMARY OF THE INVENTION

According to a first aspect of the present invention, an ultrasonic puncture needle includes a sheath, a needle tube, and a releasing mechanism, and is used in combination with an ultrasonic endoscope. The ultrasonic endoscope includes: a distal-end hard part; a bendable part which is connected to a proximal end of the distal-end hard part and which is bendable; and an operation part which performs bending operation of the bendable part. The sheath is inserted into an insertion channel of the ultrasonic endoscope so as to be capable of advancing and retreating. The needle tube is inserted into the sheath, includes an opening formed in a distal-end region thereof, and is made to puncture tissue in a body cavity. The releasing mechanism is provided on the proximal-end side of the needle tube, and releases a substance filled therein from the opening of the needle tube to the outside. Moreover, in a state in which the needle tube is disposed inside the bendable part, a periphery of the needle tube receives a force from an inner wall of the insertion channel while the bendable part is in a bent state by the operation part. The needle tube is rotated around a long axis of the insertion channel by the force, such that an axis line matching the direction of the opening in the needle tube protruding from the insertion channel becomes substantially parallel with an ultrasonic scanning face of the ultrasonic endoscope.

According to a second aspect of the present invention, in a natural state, at least a region near the distal end of the needle tube is curved smoothly in a circular arc, and a direction to visualize the largest area of the opening of the needle tube is substantially parallel with a plane formed by a circular-arc shape of the needle tube.

According to a third aspect of the present invention, an outer diameter of the needle tube is eccentric to a center of an inner cavity, and a direction to visualize the largest area of the opening of the needle tube is substantially parallel with a cross-sectional plane connecting a thinnest part and a thickest part of the needle tube.

According to a fourth aspect of the present invention, an outer-diameter cross-sectional face of the needle tube has a flat shape, and a direction to visualize the largest area of the opening of the needle tube is substantially parallel with a short-diameter cross-sectional plane of the flat shape of the needle tube.

According to a fifth aspect of the present invention, in a natural state, at least the region near the distal end of the needle tube is curved smoothly in a circular arc, and a most proximal-end side of the opening of the needle tube is in a plane formed by a circular-arc shape of the needle tube.

According to a sixth aspect of the present invention, the outer diameter of the needle tube is eccentric to the center of its inner cavity, and the most proximal-end side of the opening of the needle tube is in a cross-sectional plane connecting the thinnest part and the thickest part of the needle tube.

According to a seventh aspect of the present invention, an outer-diameter cross-sectional face of the needle tube has a flat shape, and the most proximal-end side of the opening of the needle tube is in a short-diameter cross-sectional plane of the flat shape.

According to an eighth aspect of the present invention, an inner cavity cross-sectional plane of the needle tube has a flat shape, and a direction to visualize the largest area of the opening is parallel with the longitudinal direction of the flat shape.

According to a ninth aspect of the present invention, an ultrasonic reflection machining for obtaining a reflected echo is performed on a distal-end part surface of the needle tube, the pattern of the ultrasonic reflection machining around the opening being different from that in other regions.

Preferably, the distal-end region covers the distal end.

Preferably, the distal-end region covers a region near the distal end.

Preferably, the substance includes gas.

Preferably, the substance includes liquid.

Preferably, the substance includes a solid.

Preferably, the solid includes a slender elastic body.

BRIEF DESCRIPTION OF THE DRAWINGS

FIGS. 10 and 11 are overall cross-sectional views of the ultrasonic puncture needle according to the first embodiment of the present invention.

DETAILED DESCRIPTION OF THE INVENTION

Embodiments of the present invention will be explained with reference to the drawings.
(First Embodiment)

An ultrasonic puncture needle of this embodiment is used in combination with an ultrasonic endoscope.

Figure 1:
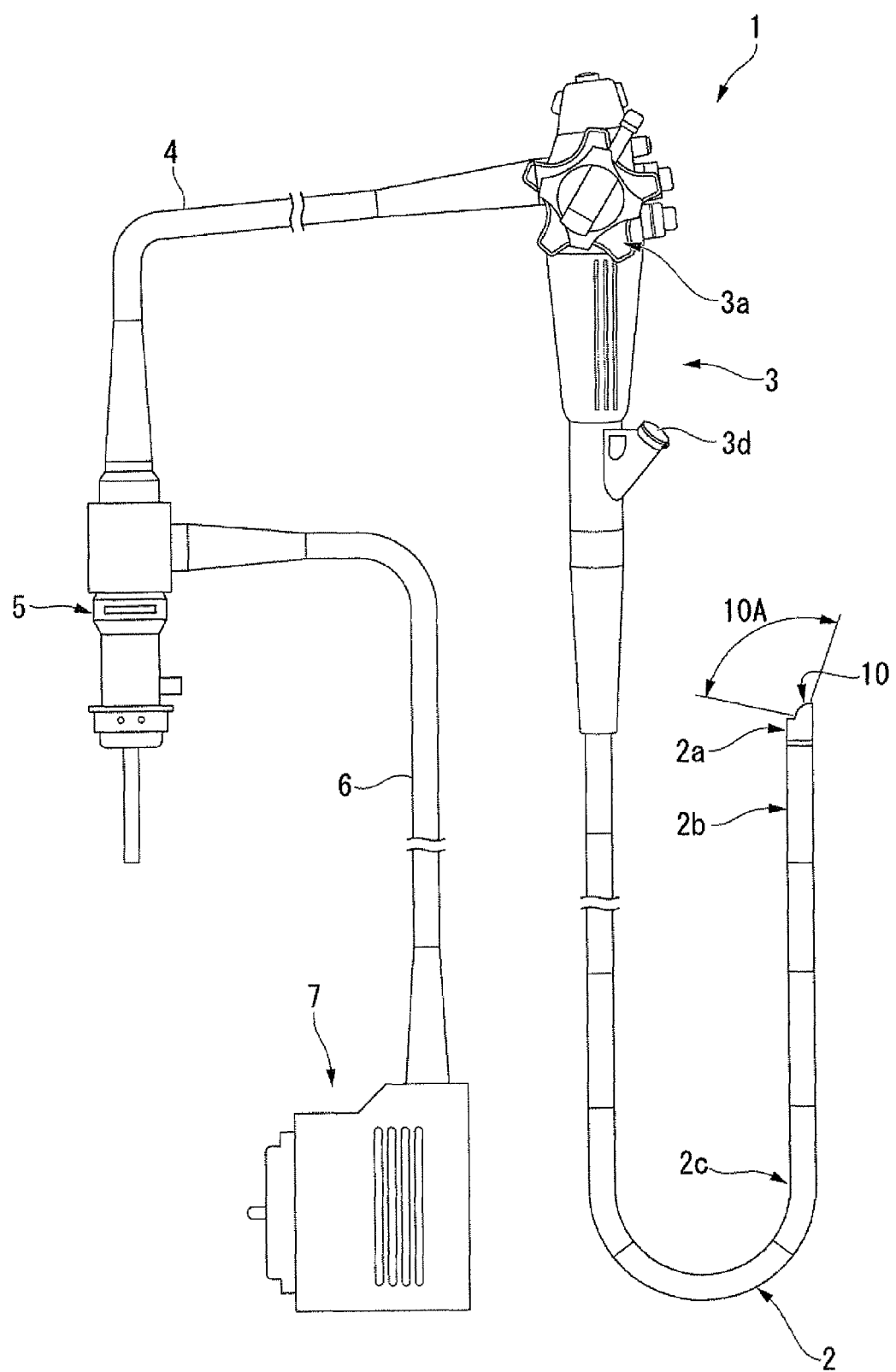
FIG. 1 is an overall view of an ultrasonic endoscope used in combination with an ultrasonic puncture needle according to a first embodiment of the present invention.
Figure 2:
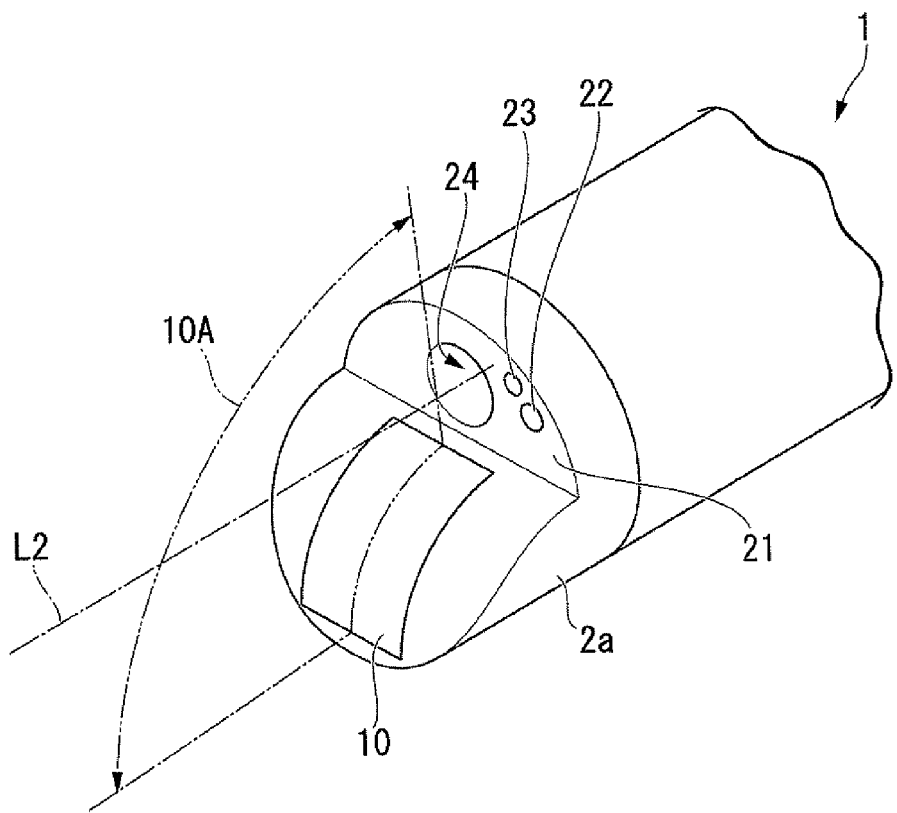
FIG. 2 is a perspective view of a distal-end part of the ultrasonic endoscope.
Figure 3:
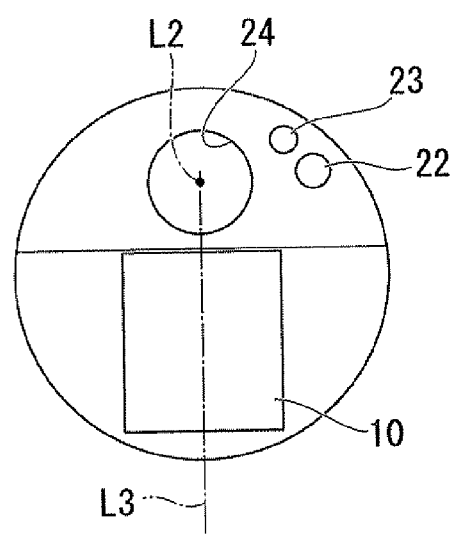
FIG. 3 is a front view of the distal-end part.
Figure 4:
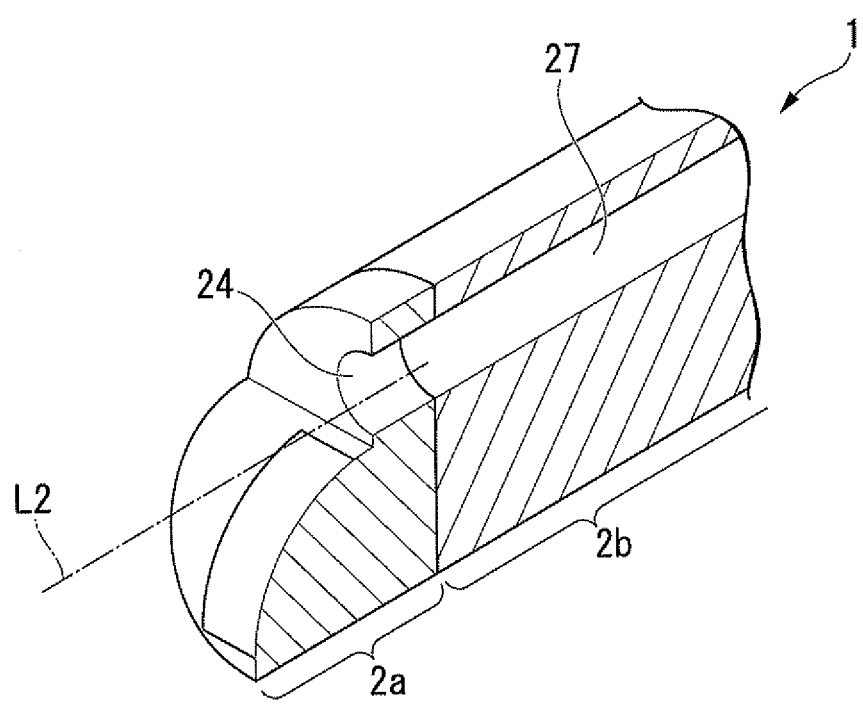
FIG. 4 is a perspective cross-sectional view of the distal-end part.

An ultrasonic endoscope of this embodiment will be explained using FIGS. 1 to 4. FIG. 1 is a view of the configuration of an ultrasonic endoscope, FIG. 2 is a perspective view of a distal-end part of the ultrasonic endoscope, FIG. 3 is a front view of the distal-end part shown in FIG. 2 when seen from the front, and FIG. 4 is a distal-end perspective cross-sectional view of the ultrasonic endoscope.

An ultrasonic endoscope 1 includes a slender insertion part 2 for being inserted into a body cavity, an operation part 3 provided at the proximal end of the insertion part 2, and a universal cord 4 that extends from a side part of the operation part 3.

An endoscope connector 5 is provided at a proximal-end part of the universal cord 4. An ultrasonic cable 6 extends from the side part of the endoscope connector 5. An ultrasonic connector 7 is provided at a proximal-end part of the ultrasonic cable 6.

The insertion part 2 includes a distal-end hard part 2a formed from a hard member, a bendable part 2b that can curve, and an elongated flexible tube part 2c that extends from the proximal end of the bendable part 2b to the distal end of the operation part 3, these being connected in that order from the distal-end side.

An ultrasonic transducer part 10 forms an ultrasonic scan plane 10A for scanning in a forward direction with respect to the insertion axis direction. In other words, the ultrasonic transducer part 10 has an ultrasonic scan plane 10A that scans in the forward direction. A signal cable (not shown) is connected to the ultrasonic transducer part 10. This signal cable extends via the insertion part 2, the operation part 3, the universal cord 4, the endoscope connector 5, and the ultrasonic cable 6, to the ultrasonic connector 7.

The ultrasonic connector 7 is connected to an ultrasonic observation device (not shown). The ultrasonic observation device exchanges signals with the ultrasonic transducer via the signal cable, converts a signal received from the ultrasonic transducer to an ultrasonic image, and displays it on a monitor (not shown).

The operation part 3 includes an angle knob 3a for executing a bending operation. The physician manipulates the angle knob 3a as appropriate, whereby a bendable wire (not shown) is pulled or loosened, and the bendable part 2b curves.

As shown in FIG. 2, the ultrasonic transducer part 10 protrudes from a distal-end face 21 of the distal-end hard part 2a of the insertion part 2. Moreover, an observation window 22 constituting the most distal-end side of an observation optical system (not shown), an illumination window 23 constituting the most distal-end side of an illumination optical system (not shown), and an insertion channel exit 24 forming the opening of a treatment tool insertion channel which a treatment tool such as a puncture needle is led through, are provided on the distal-end face 21 of the distal-end hard part 2a.

The insertion channel exit 24 is substantially parallel with the long-axis direction of the distal-end hard part 2a, and is connected to a treatment tool insertion channel (hereinafter abbreviated as 'insertion channel') 27 provided in the insertion part 2 (FIG. 4).

The observation optical system and the illumination optical system (both not shown) extend via the insertion part 2, the operation part 3, and the universal cord 4 to the endoscope connector 5. The endoscope connector 5 is connected to an endoscope observation device (not shown). The endoscope observation device transmits illuminating light from the illumination optical system to the illumination window 23, and the illuminating light illuminates the front of the distal-end hard part 2a. The endoscope observation device displays a signal arriving from the observation window 22 via the observation optical system as an observation image on a monitor (not shown). Therefore, an observation image illuminated by the illuminating light is displayed on the monitor.

The proximal-end side of the insertion channel 27 connects to a treatment tool insertion hole 3d provided in the operation part 3. The proximal-end part of the treatment tool insertion hole 3d has a luer-lock shape that allows a syringe to be connected to it. A treatment tool inserted through the treatment tool insertion hole 3d is led out from the insertion channel exit 24.

The center axis L2 of the insertion channel exit 24 is substantially parallel with the long-axis direction of the distal-end hard part 2a. The plane defined by the center axis L2 and the perpendicular direction center line L3 of the ultrasonic transducer part 10 has a configuration that substantially matches that of the ultrasonic scan plane 10A. Since a treatment tool led out from the insertion channel exit 24 is led out onto the ultrasonic scan plane 10A, it is visibly displayed on the ultrasonic image.

Figure 5:
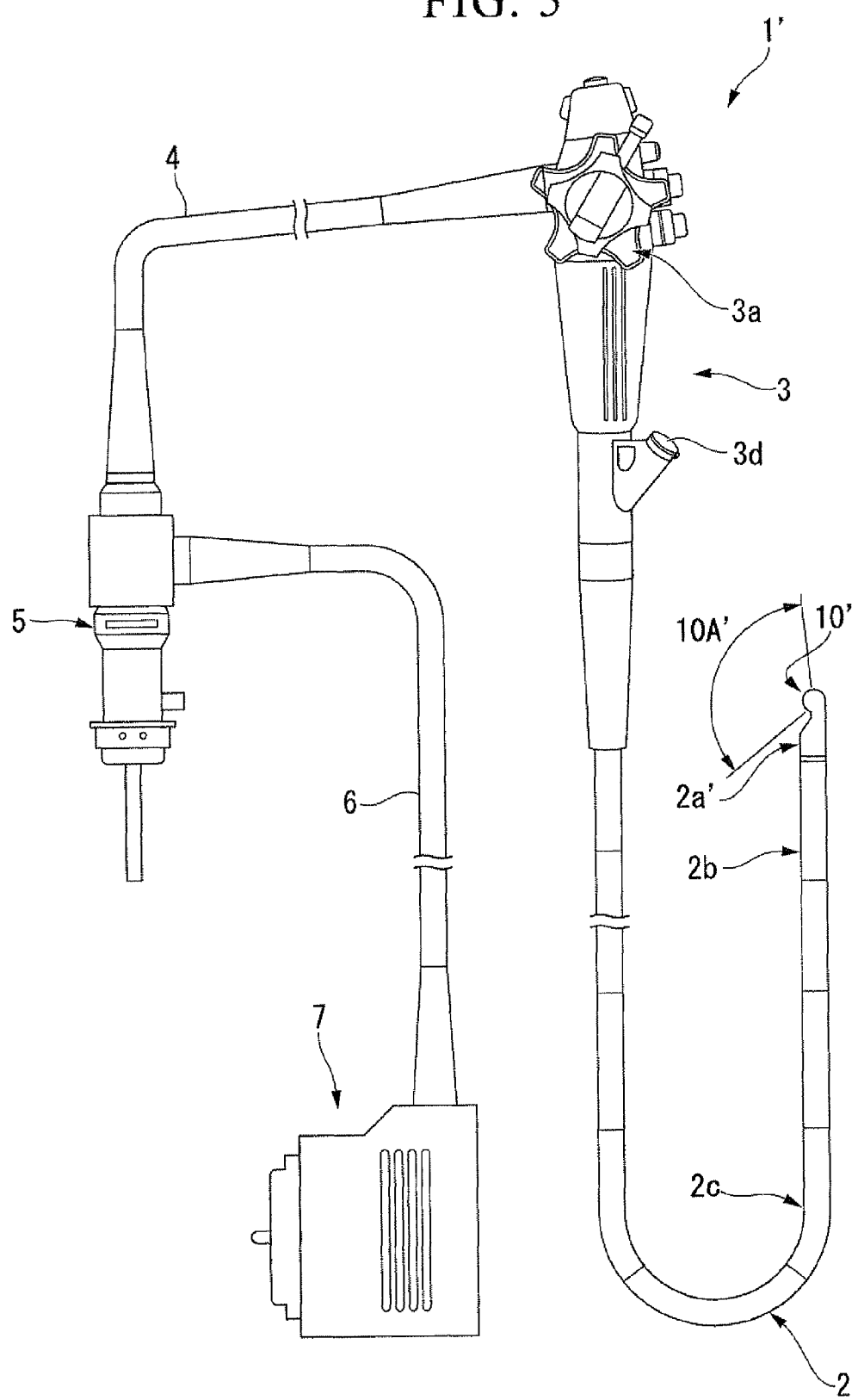
FIG. 5 is an overall view of another ultrasonic endoscope used in combination with the ultrasonic puncture needle according to the first embodiment of the present invention.
Figure 7:
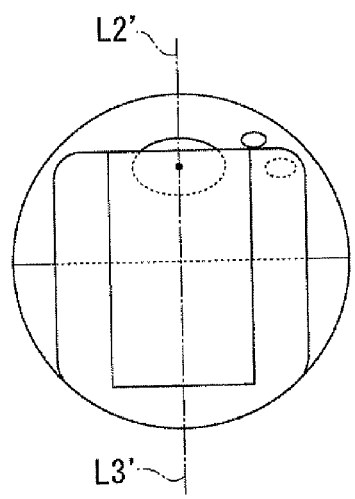
FIG. 7 is a front view of the distal-end part.
Figure 8:
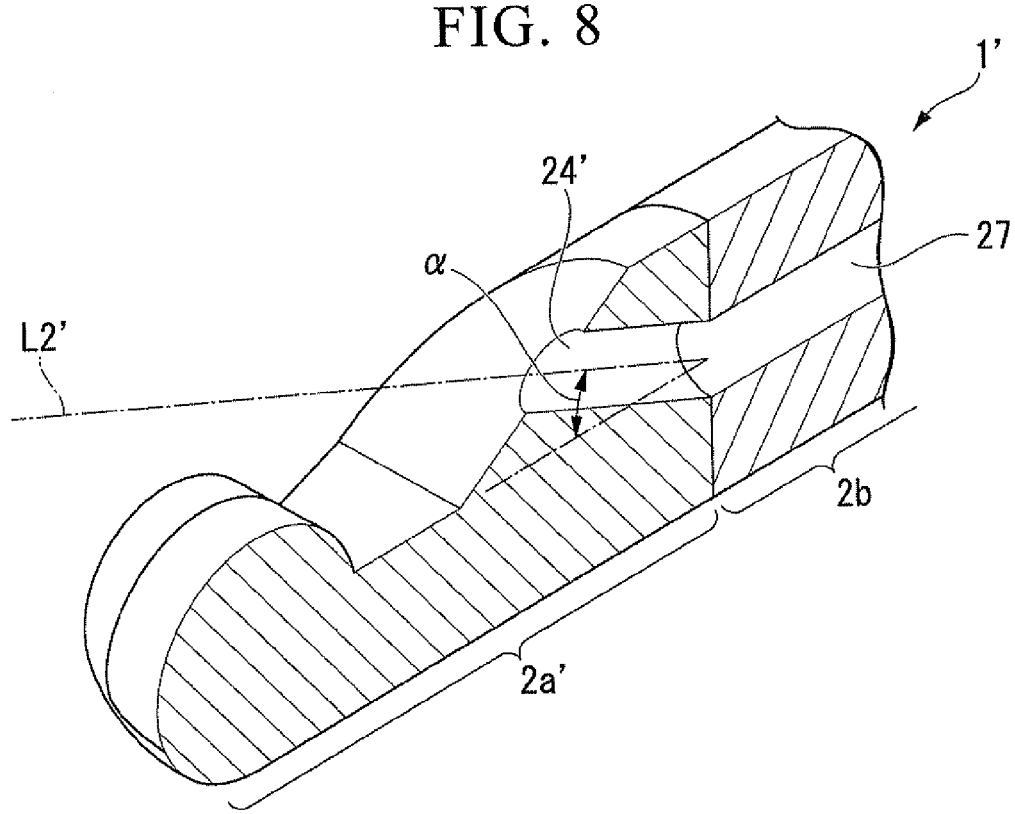
FIG. 8 is a perspective cross-sectional view of the distal-end part.

Another ultrasonic endoscope that can be used in this embodiment will be explained using FIGS. 5 to 8. FIG. 5 is a view of the configuration of an ultrasonic endoscope 1', FIG. 6 is a perspective view of a distal-end part of the ultrasonic endoscope 1', FIG. 7 is a front view of the distal-end part when seen from the front face, and FIG. 8 is a distal-end perspective cross-sectional view of the ultrasonic endoscope 1'.

In the ultrasonic endoscope 1', sections having a configuration similar to that of the ultrasonic endoscope 1 described above are designated with like reference numerals in FIGS. 5 to 8. A point of difference with the ultrasonic endoscope 1 is that the ultrasonic transducer part 10' at the distal end is larger. As a result, the ultrasonic scan plane 10A' that scans in a forward direction with respect to the insertion axis direction has a wider field of view.

Figure 6:
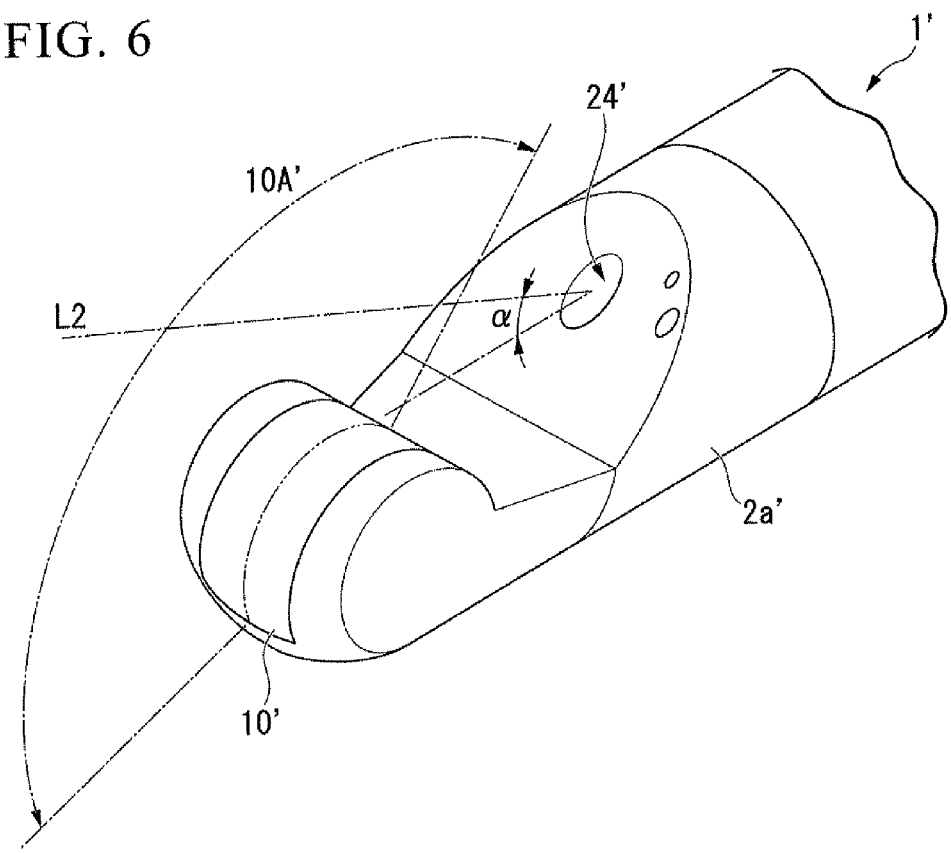
FIG. 6 is a perspective view of a distal-end part of the ultrasonic endoscope according to the first embodiment of the present invention.

Moreover, as shown in FIG. 6, the insertion channel exit 24' of the ultrasonic endoscope 1' is tilted at an angle α with respect to the long-axis direction of the distal-end hard part 2a', such that the treatment tool led out from the insertion channel exit does not make contact with the large ultrasonic transducer part 10'.

However, as in the ultrasonic endoscope 1, the plane defined by the center axis L2' of the insertion channel exit 24' and the perpendicular direction center line L3 of the ultrasonic transducer part 10' is configured such that it substantially matches the ultrasonic scan plane 10A'. The treatment tool led out from the insertion channel exit 24' is therefore led out onto the ultrasonic scan plane 10A' and visibly displayed on the ultrasonic image.

Figure 9:
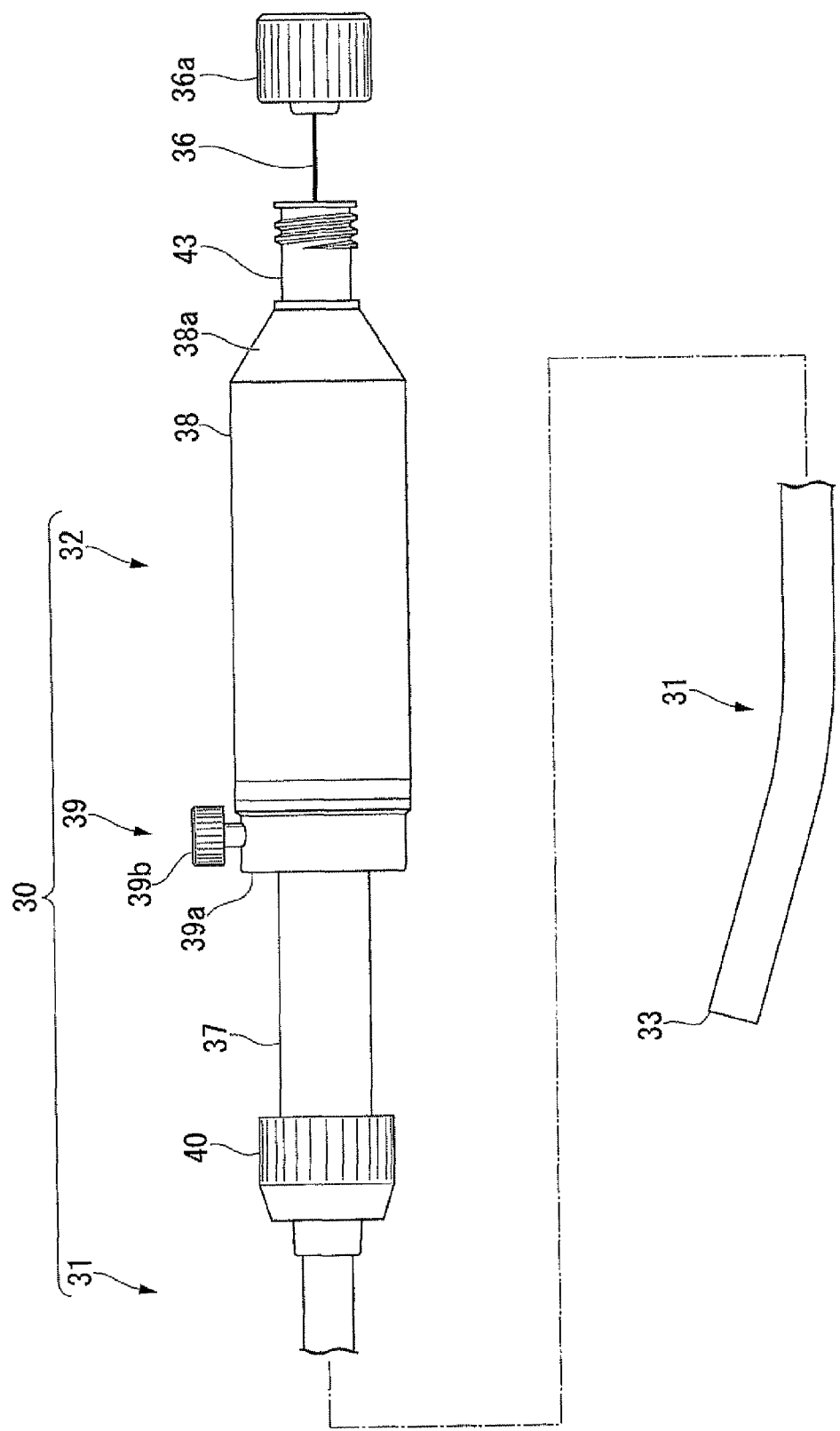
FIG. 9 is an overall exterior view of the ultrasonic puncture needle according to the first embodiment of the present invention.
Figure 10:
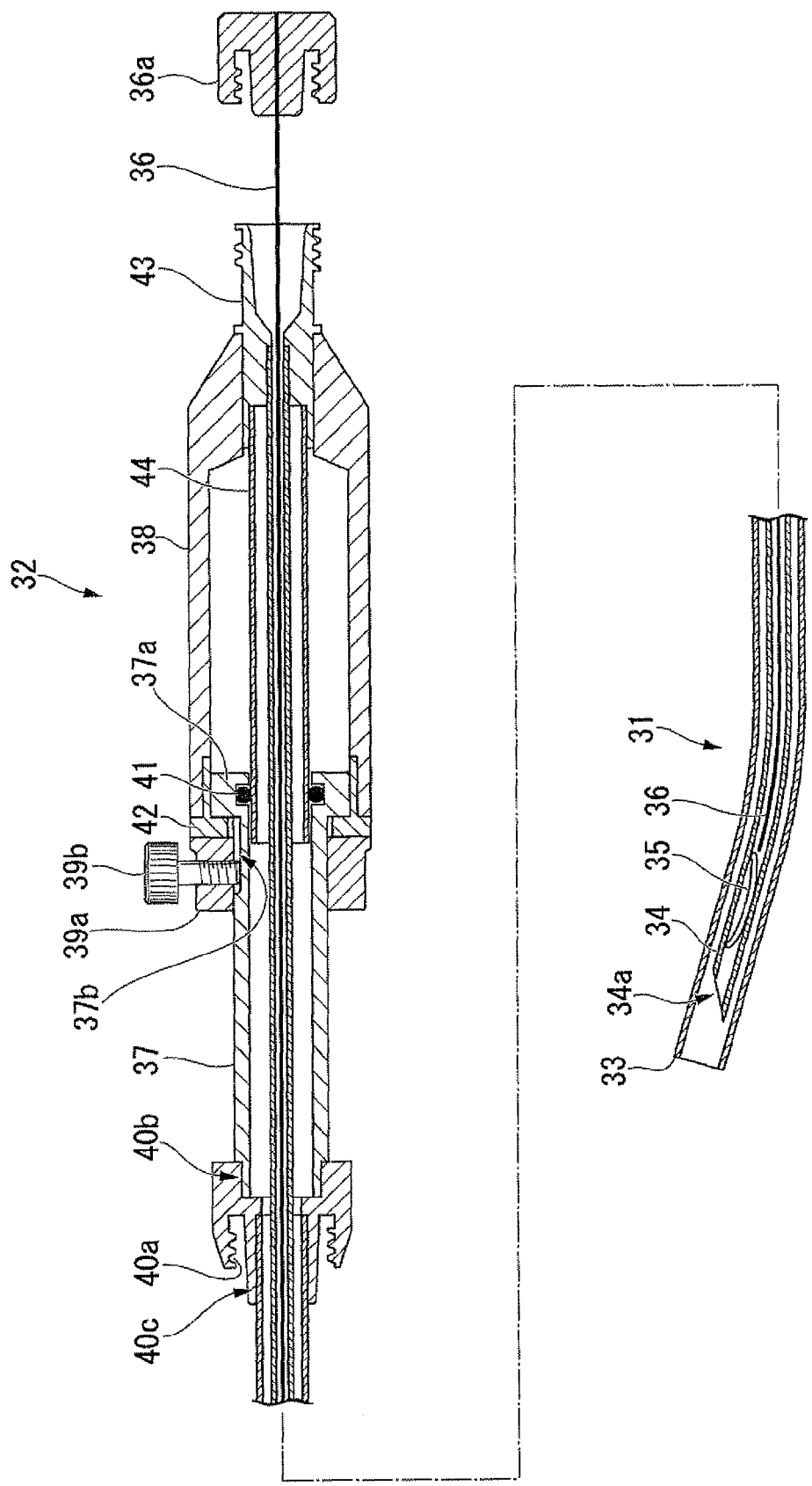

Subsequently, an ultrasonic puncture needle of this embodiment will be explained using FIGS. 9 to 14B. FIG. 9 is an overall exterior view of the ultrasonic puncture needle, FIGS. 10 and 11 are overall cross-sectional views, FIGS. 12 and 13 are views for explaining the shape of a needle tube, and FIG. 14 is an explanatory view of an implant.

An ultrasonic puncture needle 30 of this embodiment includes an insertion part 31 and an operation part 32. The insertion part 31 is the section that is inserted into the insertion channel 27 of the ultrasonic endoscope 1. The operation part 32 is provided at the proximal-end part of the insertion part 31, and is secured to the treatment tool insertion hole 3d of the ultrasonic endoscope 1.

Each part of the insertion part 31 will be explained.

A sheath 33 is a flexible tube, and is disposed on the outermost side of the insertion part 31. A resin such as, for example, polyetheretherketone, polyethersulfone, or Teflon (Registered Trademark) is suitable as the material for the sheath 33. Alternatively, a metal wire conventionally known as a flexible shaft, particularly a wound metal formed by winding a stainless steel wire in the shape of a coil spring, is suitable as the material for the sheath 33. A needle tube 34 is inserted into an inner cavity of the sheath 33, preventing the needle tube 34 and the insertion channel 27 from being damaged by direct contact between the needle tube 34 and the inner face of the insertion channel 27.

The needle tube 34 is formed from, for example, a slender and thin stainless steel pipe or such like, and has a sharp distal end. The needle tube 34 is inserted into the sheath 33 such that it can advance/retreat.

FIGS. 12A to 13B show the region near the distal end of the needle tube 34 in greater detail. When the needle tube 34 is in a natural state, at least the region near the distal end is curved smoothly in a circular arc. While the most distal end of the needle tube 34 is not curved in a circular arc in the example shown here, it can be included within the section that is curved in a circular arc.

The distal end of the needle tube 34 is cut into a diagonal shape like a conventional syringe, and an inner cavity is open in the diagonally cut face. The direction perpendicular to the distal-end face, i.e. the direction to visualize the largest area of the opening 34a (indicated by arrow A1 in FIG. 12A), is substantially parallel with the plane 34b that contains the long center axis of the needle tube 34. A point 34d at the most proximal-end side of the opening 34a is coplanar with the plane 34b.

Figure 12A:
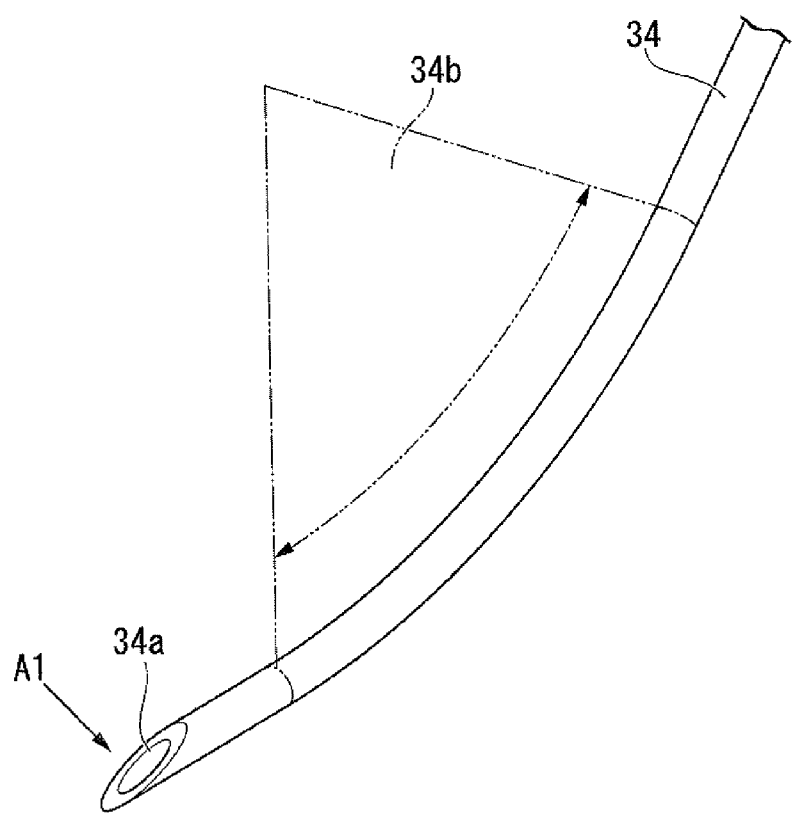
FIGS. 12A and 12B are views of the distal-end side of a needle tube of the ultrasonic puncture needle according to the first embodiment of the present invention.
Figure 12B:
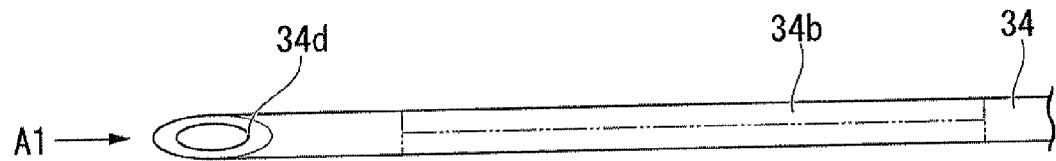
Figure 13A:
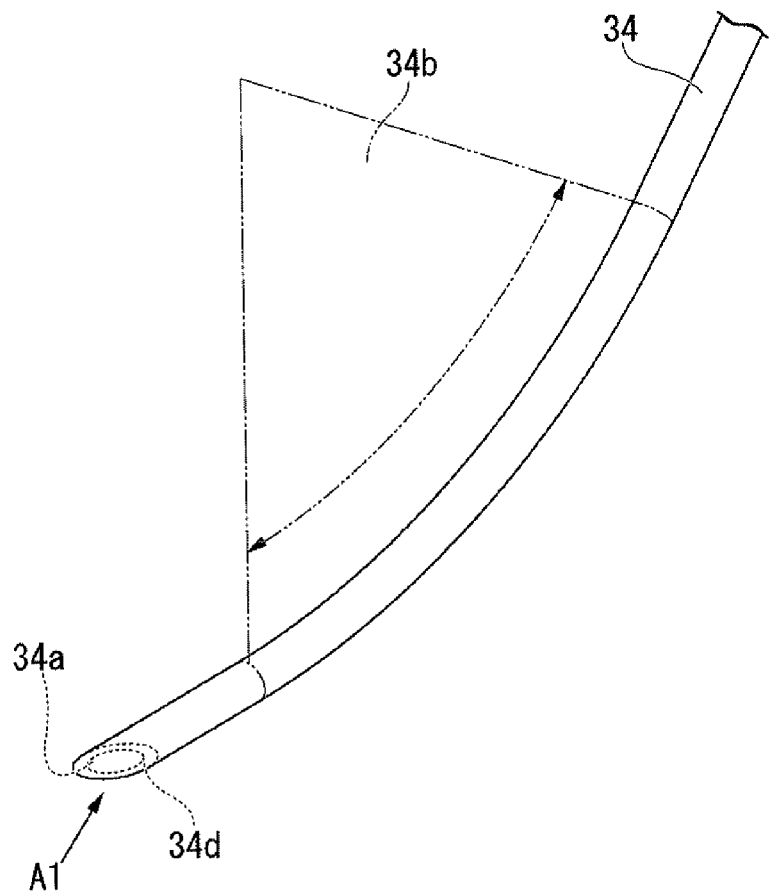
FIGS. 13A and 13B are views of the distal-end side of another example of the needle tube according to the first embodiment of the present invention.
Figure 13B:
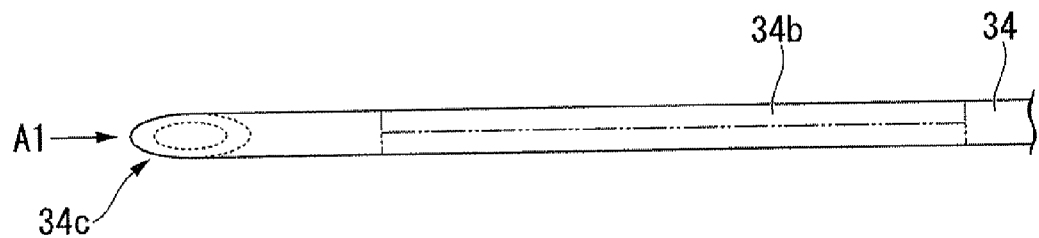

In the example shown in FIGS. 13A and 13B, the distal end of the needle tube 34 is cut in the reverse direction to the example shown in FIGS. 12A and 12B; either can be selected depending on the objective.

An implant 35 is a metal piece containing a substance that generates very weak radiation for treatment purposes.

Figure 14A:
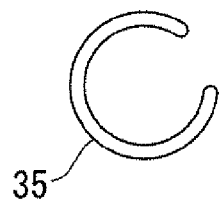
FIG. 14A is a view of an implant stored in the needle tube according to the first embodiment and a sixth embodiment of the present invention.
Figure 14B:
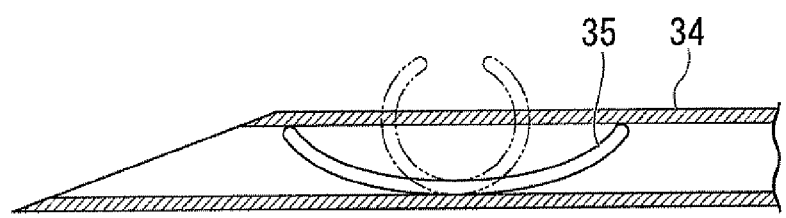
FIG. 14B is a view of a state where the implant has been stored in the needle tube according to the first embodiment of the present invention.

FIGS. 14A and 14B show the implant 35 in greater detail. Its shape is formed by bending a rod-like material that is more slender than the inner cavity of the needle tube 34, obtaining a rod spring with elasticity. The implant 35 filled into the tip of the inner cavity of the needle tube 34 has elasticity, and thus pushes the inner wall of the needle tube 34 with a force of attempting to return to its former shape. Therefore, it is not easily dislodged from the needle tube 34.

A stylet 36 is a slender wire made from, for example, stainless steel or nickel titanium. The stylet 36 is disposed on the proximal-end side of the needle tube 34 inner cavity so that it can be inserted and removed, and, by an operation described below, pushes the implant 35 out from the needle tube 34.

Constitutive elements of the operation part 32 will be explained.

An operation-part main unit 37 is formed from a resin member.

A slider 38 can slide with respect to the operation-part main unit 37, and is formed from a resin member.

A stopper 39 can be set at a desired value according to a result of measuring the sliding distance of the slider 38 with respect to the operation-part main unit 37, and is configured as follows. A stopper member 39a can slide with respect to the operation-part main unit 37, and is made from a material such as resin. A fixing screw 39b is screwed into the stopper member 39a for fixing the stopper member 39a in a desired position, and is made from metal or a hard resin.

The operation-part main unit 37 is shaped like a slender pipe, with a flange part 37a at its proximal-end part and a resin connection part 40 adhesively fixed to its distal-end part, the proximal-end part of the sheath 33 being fixed to this connection part 40. On the distal-end side of the connection part 40, a screw 40a is fixed by connection to the treatment tool insertion hole 3d of the ultrasonic endoscope 1, and the proximal-end part includes a recess 40b for providing the distal-end part of the operation-part main unit 37. The sheath 33 is fixed to a connection part 40c formed in the connection part.

A recess is formed in the inner peripheral face of the flange part 37a. An O-ring 41 is disposed in the recess in the flange part 37a, and holds a guide pipe described below. A notched step 37b is formed at a predetermined position on the outer peripheral face further to the distal-end side than the flange part 37a, and has a flat-faced part that the fixing screw 39b contacts.

At the time of manufacture and shipment of the ultrasonic puncture needle 30, the distal-end face of the fixing screw 39b is contacted the flat-faced part of the notched step 37b at a predetermined torque, whereby the slider 38 is arranged on the proximal-end side of the operation-part main unit 37.

In this arrangement state, the distal-end parts of the needle tube 34 and the stylet 36 are inside the sheath 33. Even if the slider 38 is moved to the distal-end side due to some kind of external force, the side part of the fixing screw 39b contacts the rising part of the notched step 37b and stops the slider 38 from moving toward the distal-end side. In this contacting state, the distal-end parts of the needle tube 34 and the stylet 36 do not, of course, protrude from the distal end of the sheath 33.

When the fixing screw 39b is loosened, it can slide on the operation-part main unit 37 in the longitudinal direction. The maximum movable distance of the slider can be set by sliding the stopper member 39a to a given position, and fixing it by screwing in the fixing screw 39b.

The slider 38 is shaped like a pipe with a small-diameter part 38a at its proximal-end part. A sliding arrangement member 42 is adhesively fixed to the distal-end part of the slider 38 to arrange the slider 38 so that it can slide with respect to the operation-part main unit 37.

A resin ferrule member 43 is disposed in the proximal-end opening part of the slider 38. The proximal-end part of the needle tube 34, and the proximal-end part of a guide pipe 44 having a distal-end part held by the O-ring 41, are fixed to the distal-end part of the ferrule member 43. The proximal-end part of the ferrule member 43 has a luer-lock shape that allows a syringe or the like to be connected to it.

The stylet 36 is inserted from the ferrule member of the slider 38. A resin knob 36a is provided in a single piece at the proximal-end part of the stylet 36.

After assembling the various constitutive members of the ultrasonic puncture needle 30 having the above configuration, it is stored in a sterilization bag (not shown) and disinfected.

An operation of the disposable type of ultrasonic puncture needle 30 having the configuration described above will be explained. A case where the ultrasonic endoscope 1 shown in FIGS. 1 to 4 is combined with the needle tube 34 shown in FIGS. 12A and 12B will first be explained, followed by a case that functions in exactly the same way by using the ultrasonic endoscope 1' shown in FIGS. 5 to 8 and the needle tube 34 shown in FIGS. 13A and 13B.

Firstly, the physician removes the ultrasonic puncture needle 30 from a sterilization bag (not shown) which it was being stored in. The physician then inserts the sheath 33 from the treatment tool insertion hole 3d of the ultrasonic endoscope 1 into the insertion channel 27, screws the screw 40a on the connection part 40 of the operation part 32 into the treatment tool insertion hole 3d, and thus fixes the ultrasonic puncture needle 30 to the ultrasonic endoscope 1.

As a result, an ultrasonic image of the distal-end part of the sheath 33 is clearly depicted on an ultrasonic observation image of the target region. Here, the physician sets the positional relationship between the distal end of the sheath 33 and the target region, and then measures the distance between them.

Subsequently, the physician loosens the fixing screw 39b, and slides the stopper member 39a on the operation-part main unit 37 in correspondence with the above-mentioned distance. When the physician has moved the stopper member 39a to a predetermined position, the physician tightens the fixing screw 39b.

Thereafter, the physician grips the slider 38, and moves it rapidly toward the stopper 39. The tip of the needle tube 34 thus reliably pierces the target region.

After checking that the needle tube 34 has reached the target region, the physician pushes the knob 36a of the stylet 36 to the distal-end side. The implant 35 is delivered from the opening 34a at the needle tube 34 tip, and is deposited inside the body.

To deposit the implant 35 accurately in the target region, the physician must check the implant 35 on the ultrasonic observation image while the physician delivers it. Accordingly, in this invention, the angular position of the needle tube 34 around the axis is controlled so as to match the direction of delivering the implant 35 with the ultrasonic scan plane. A method of matching the direction of delivering the implant 35 with the ultrasonic scan plane will be explained below.

Figure 15:
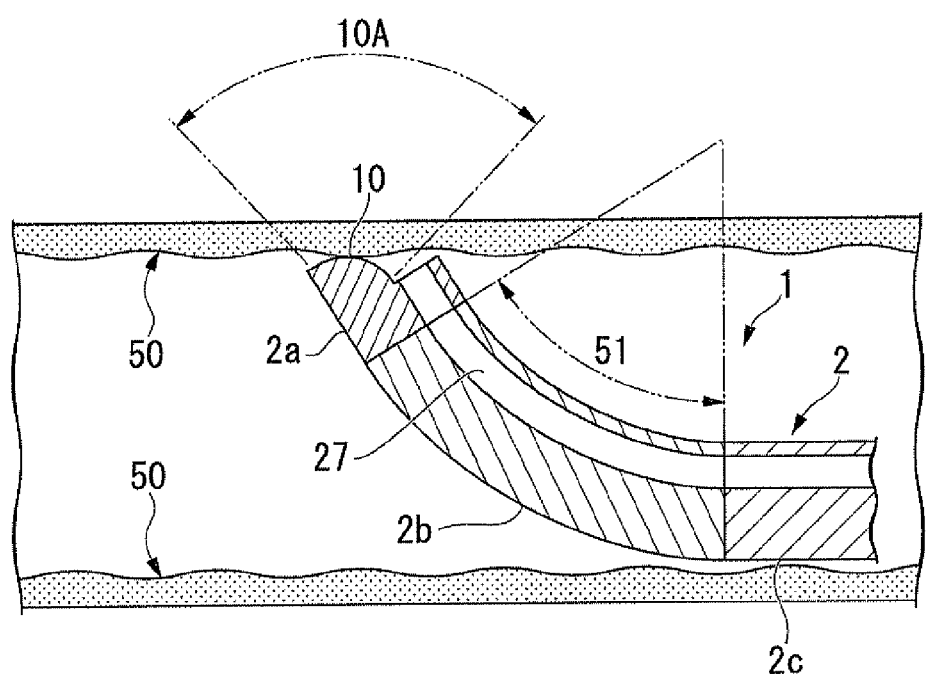
FIG. 15 is a view of an operation of an ultrasonic endoscope when the ultrasonic puncture needle according to the first embodiment of the present invention is being used.

Since ultrasonic waves attenuate severely in air, during ultrasonic observation, the ultrasonic transducer part 10 disposed at the distal end of the ultrasonic endoscope 1 must be brought firmly into contact with the body tissue. In FIG. 15, since the ultrasonic endoscope 1 is inserted into the body-cavity tissue 50, to bring the ultrasonic transducer 10 firmly into contact with the tissue, the bendable part 2b of the insertion part 2 must be curved in the direction normally termed 'up' and directed toward the body-cavity tissue 50. When it has been curved, the bendable part 2b is shaped substantially like a circular arc, and, naturally, so is the insertion channel 27 disposed inside it. The plane 51 containing the long center axis of the insertion channel 27 is now substantially coplanar with the ultrasonic scan plane 10A.

Figure 16A:
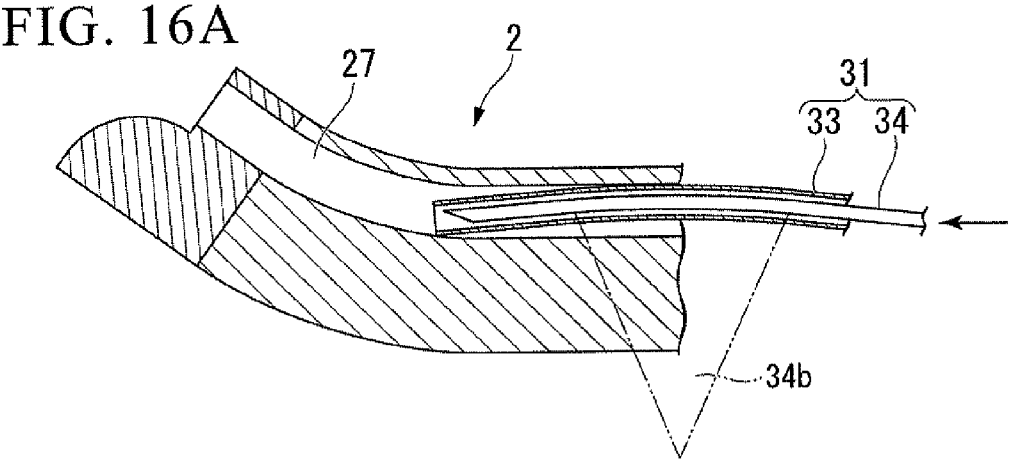
FIGS. 16A to 16C are views of an operation of the ultrasonic puncture needle according to the first embodiment of the present invention in a curved ultrasonic endoscope.
Figure 16B:
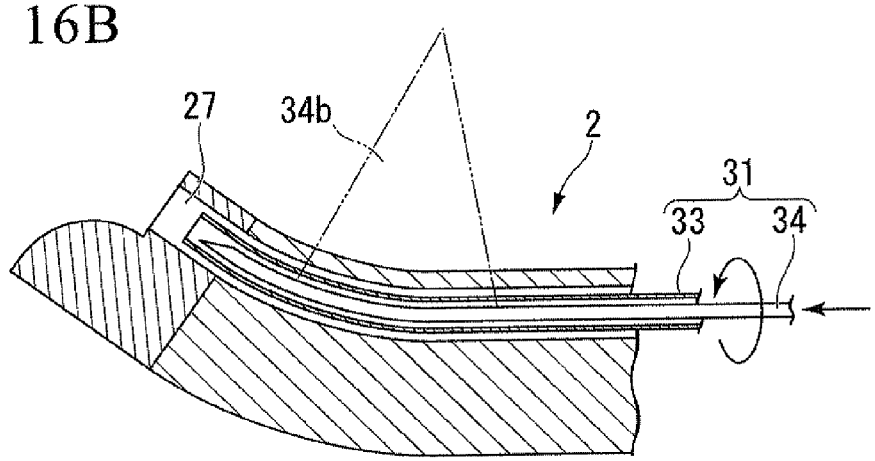
Figure 16C:
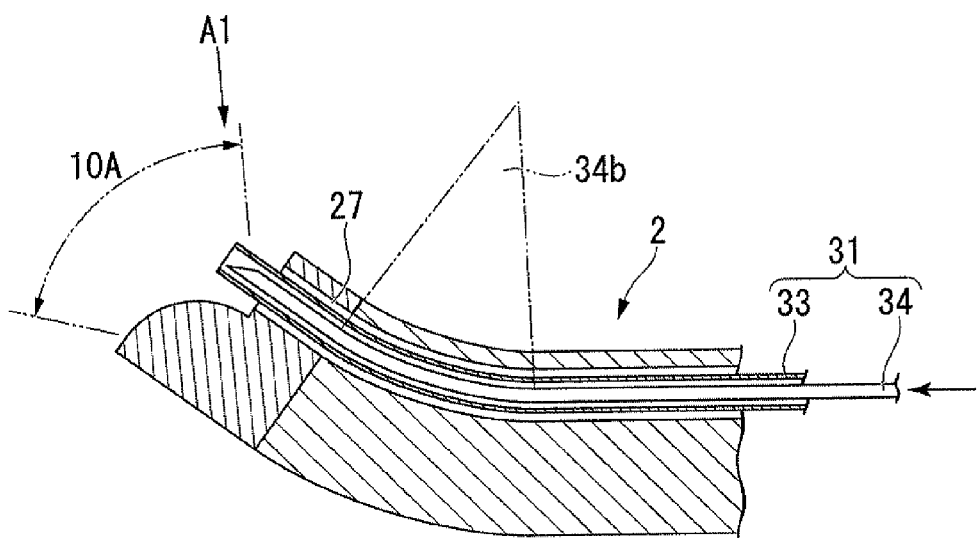

FIGS. 16A to 16C illustrate the state of the insertion part 31 of the ultrasonic puncture needle 30, including the needle tube 34 with the section near its distal end curved smoothly in a circular-arc shape, being passed through the curved insertion channel 27 in chronological sequence of the operation. In FIG. 16A, the distal end of the insertion part 31 has been pushed to just before the curved part of the insertion channel 27 of the ultrasonic endoscope 1. When the insertion part 31 is pushed further, as shown in FIG. 16B, the circular-arc shape of the needle tube 34 attains the curved shape of the insertion part 2. As it is inserted, the needle tube 34 receives a force from the inner wall of the insertion channel 27, and the needle tube 34 is consequently made to rotate around the long axis, such that the circular-arc shape of the insertion channel 27 and the circular-arc shape of the needle tube 34 are coplanar (including substantially coplanar). As a result, the plane 34b containing the long center axis of the needle tube 34 (i.e. the plane containing an axis that matches the direction of the opening in the needle tube 34) becomes the same as the plane 51 containing the long center axis of the insertion channel 27. Therefore, the plane 34b becomes substantially coplanar with the ultrasonic scan plane 10A.

FIG. 16C illustrates the state when the insertion part 31 has reached the predetermined position. While the angular position of the needle tube 34 around the axis is unchanged from that in FIG. 16B, the length of the overlap between the circular-arc shape of the needle tube 34 and the curved shape of the insertion part 2 increases, and the angular position of the needle tube 34 around the axis is therefore more stable. Since the direction A1 for visualizing the largest area of the opening 34a is substantially parallel with the plane 34b, the direction A1 becomes substantially parallel with the ultrasonic scan plane 10A. In other words, the axis matching the direction of the opening in the needle tube 34 becomes substantially parallel with the ultrasonic scan plane 10A.

Figure 17:
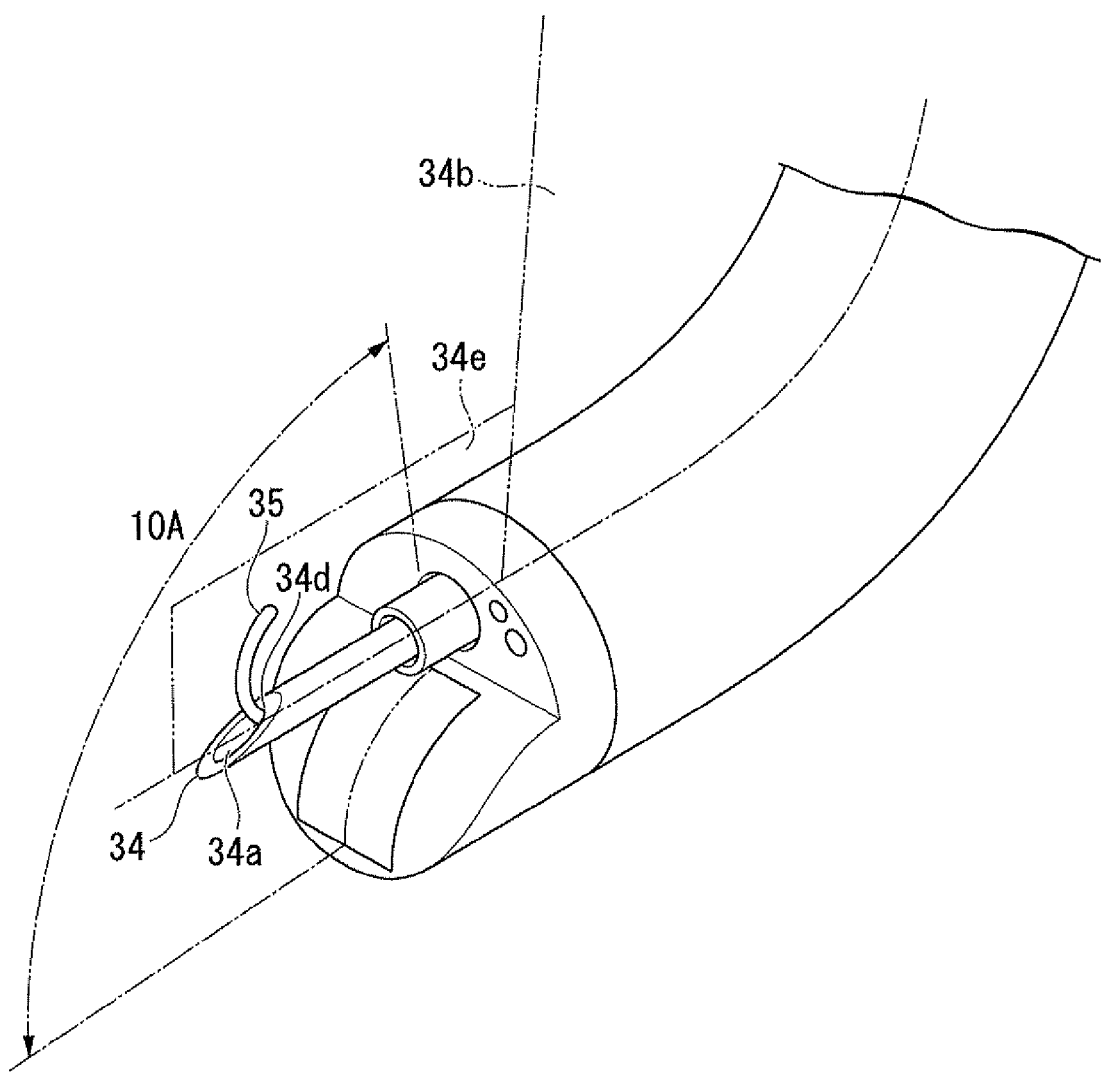
FIG. 17 is a view of a state where an implant has been delivered from the ultrasonic puncture needle according to the first embodiment of the present invention.

As mentioned earlier, the implant 35 has elasticity, and is an extended state while being stored inside the needle tube 34. As shown in FIG. 17, when the implant 35 is delivered from the opening 34a of the needle tube 34, it attempts to return from the extended state to its original shape, and consequently rubs against the point 34d at the most proximal-end side of the opening 34a as it is delivered. The implant 35 is now delivered within a plane 34e, which is substantially the same as the plane 34b and contains the proximal-end point 34d.

Since the plane 34b is substantially the same as the ultrasonic scan plane 10A, the implant 35 can be favorably confirmed on the ultrasonic image.

Subsequently, a case using the ultrasonic endoscope 1' shown in FIGS. 5 to 8 and the needle tube 34 shown in FIGS. 13A and 13B will be explained.

Figure 18:
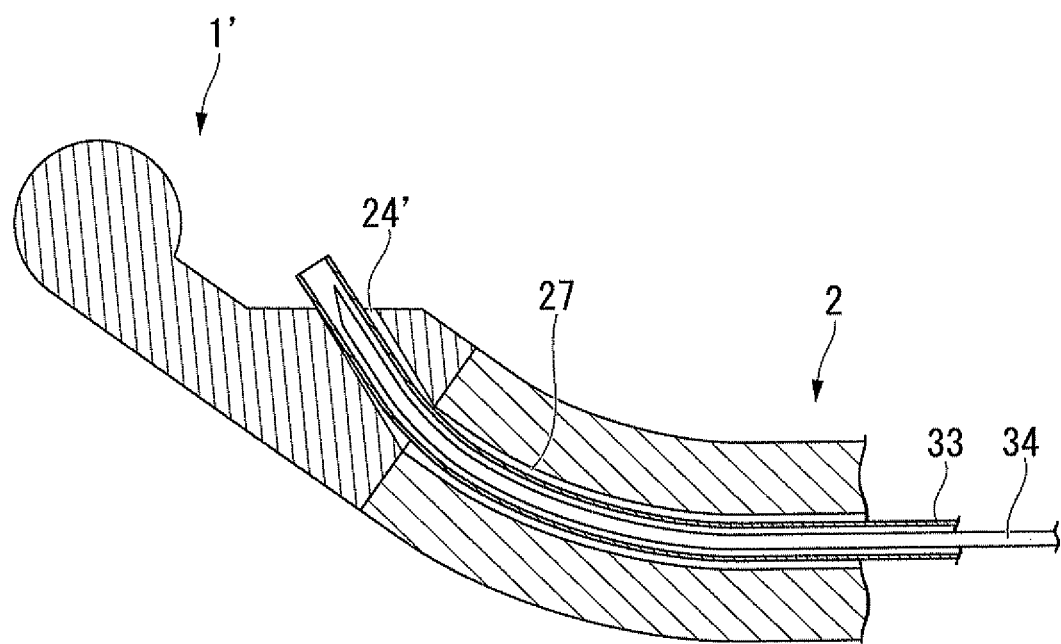
FIG. 18 is a view of a state where the ultrasonic puncture needle according to the first embodiment of the present invention has been inserted into the ultrasonic endoscope.

FIG. 18 is a state where the insertion part 31 of the ultrasonic puncture needle 30, including the needle tube 34 with a part near the distal-end that, in a natural state, is curved in a circular-arc shape, has been passed along the curved insertion channel 27, and the insertion part 31 has reached a predetermined position.

As shown in FIG. 6, the insertion channel exit 24' tilts at an angle α with respect to the long-axis direction of the distal-end hard part 2a', such that the treatment tool led out from the insertion channel exit does not make contact with the large ultrasonic transducer part 10'. As shown in FIG. 15, during the actual procedure, the bendable part 2b of the endoscope insertion part 2 is curved in the direction normally termed 'up'. It is clear that, in this state, the needle tube 34 curved in a circular-arc shape can be smoothly passed through the insertion channel exit 24' and the cavity formed by the insertion channel 27. Therefore, when the implant 35 is delivered from the opening 34a of the needle tube 34, it can be favorably confirmed on the ultrasonic image.

Of course, when the ultrasonic endoscope 1 shown in FIGS. 1 to 4 is used in combination with the needle tube shown in FIGS. 13A and 13B, and when the ultrasonic endoscope 1' shown in FIGS. 5 to 8 is used in combination with the needle tube shown in FIGS. 12A and 12B, similar functions are achieved.

After the implant 35 has been removed from the body, the ultrasonic puncture needle 30 is detached from the ultrasonic endoscope and destroyed, and this series of procedures ends.
(Second Embodiment)

In the first embodiment, a case was described where a solid implant is deposited inside a body. An alternative case where a gaseous or liquid medicine is injected into the body will be explained as a second embodiment. In the following description, sections similar to those in the configuration of the first embodiment will not be repetitiously explained, and only points of difference will be explained.

Figure 19:
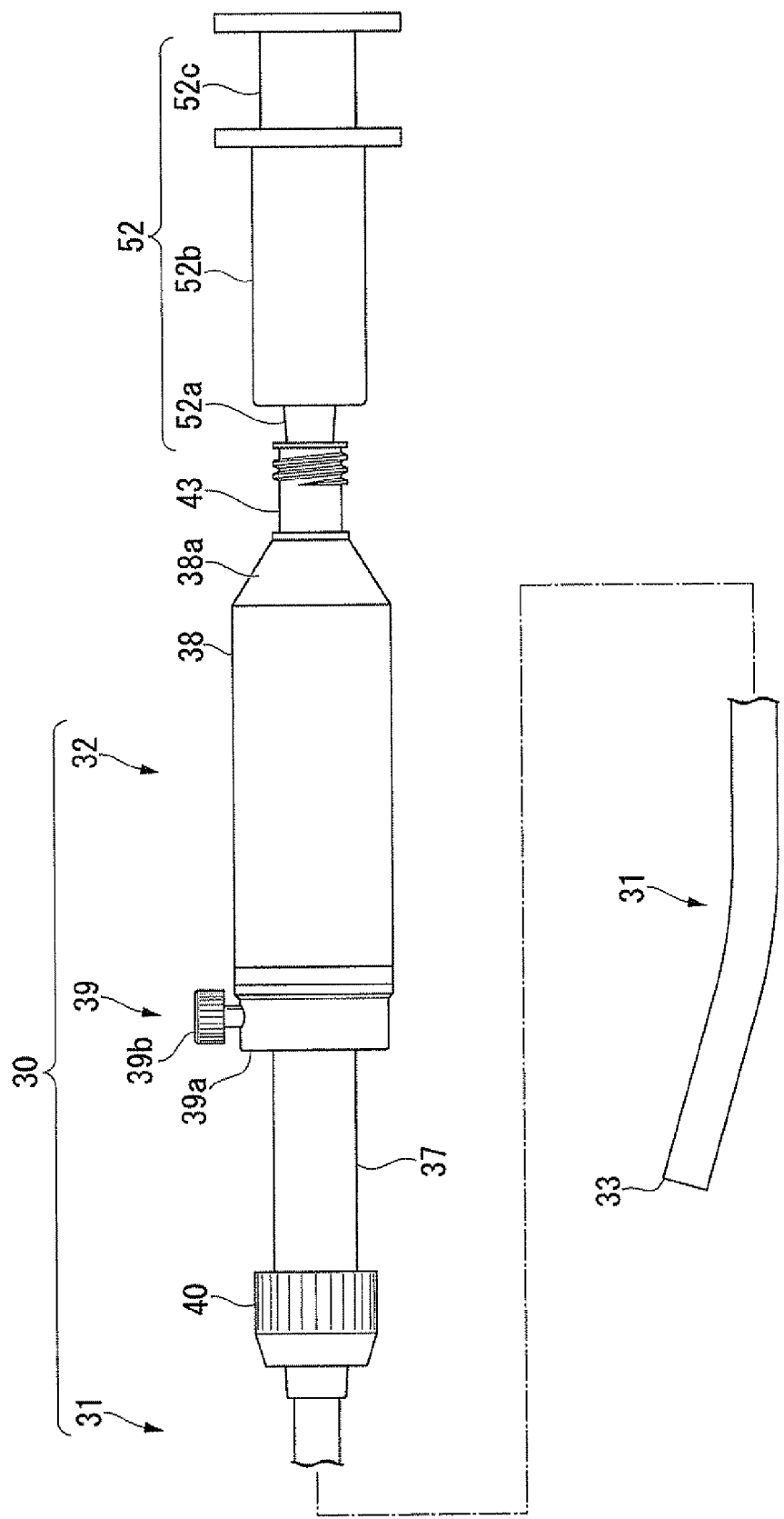
FIG. 19 is an overall schematic view of an ultrasonic puncture needle according to a second embodiment of the present invention.
Figure 20:
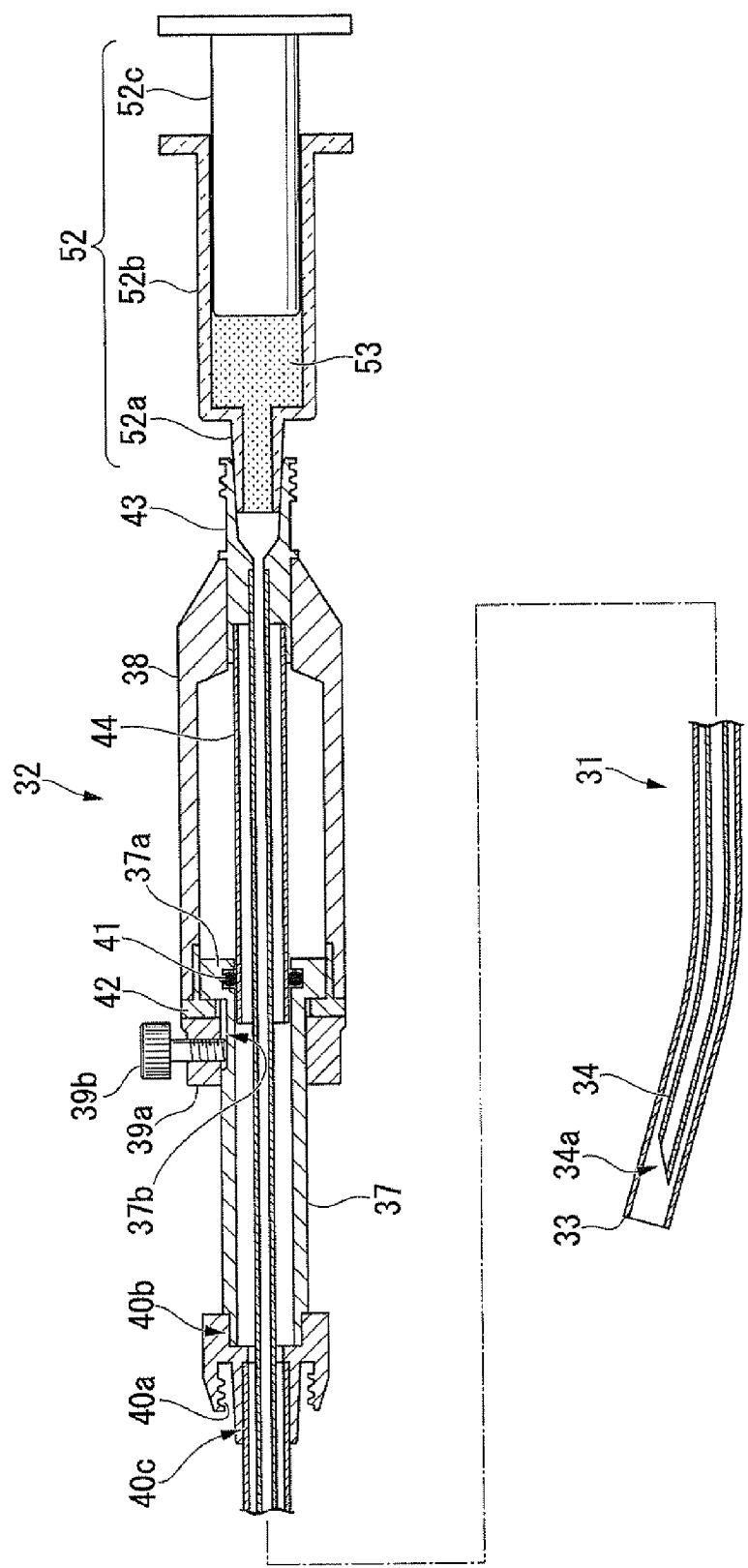
FIG. 20 is an overall cross-sectional view of the ultrasonic puncture needle according to the second embodiment of the present invention.

FIG. 19 is an overall schematic view of an ultrasonic puncture needle, and FIG. 20 is an overall cross-sectional view of the same ultrasonic puncture needle.

An injection syringe 52 is attached to a resin ferrule member 43. The injection syringe 52 includes a cylinder ferrule 52a, a cylinder 52b, and a piston 52c. The cylinder 52b is filled with a gaseous or liquid medicine 53.

The mechanism for controlling the angular position of the needle tube 34 around the axis is similar to that of the first embodiment, and will not be repetitiously explained.

When the piston 52c of the injection syringe 52 is pressed, a medicine 53 passes along the inner cavity of the needle tube 34 and is released into the body from the opening 34a, whereby the medicine 53 is released onto the ultrasonic scan plane 10A. Therefore, it is possible to favorably confirm on the ultrasonic image that the medicine 53 is being delivered.
(Third Embodiment)

A configuration in which the distal-end shape of the needle tube differs from that of the first and the second embodiments will be explained as a third embodiment. In this embodiment, the substance being delivered into the body can be a solid such as the implant 35, or it can be a gas or liquid such as the medicine 53. Other than the distal-end shape of the needle tube, the ultrasonic puncture needle in this embodiment has the same configuration as the first embodiment when delivering a solid, and has the same configuration as the second embodiment when delivering a gas or liquid such as the medicine 53. Therefore, only points of difference will be described.

Figure 21A:
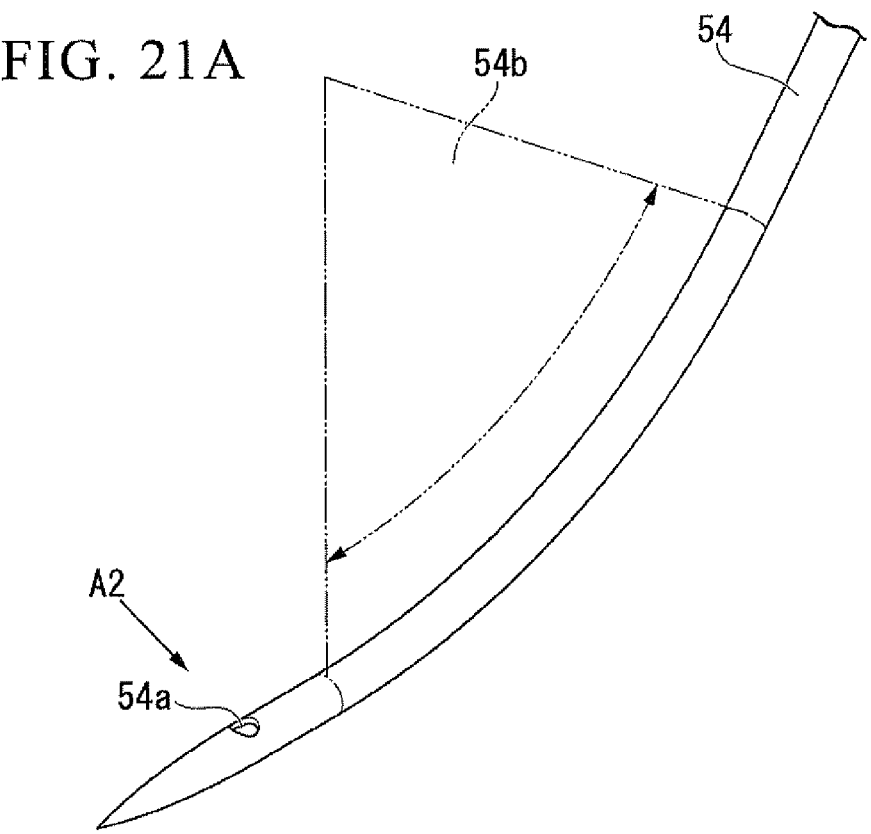
FIGS. 21A to 21C are views of the distal-end side of a needle tube of an ultrasonic puncture needle according to a third embodiment of the present invention.
Figure 21B:
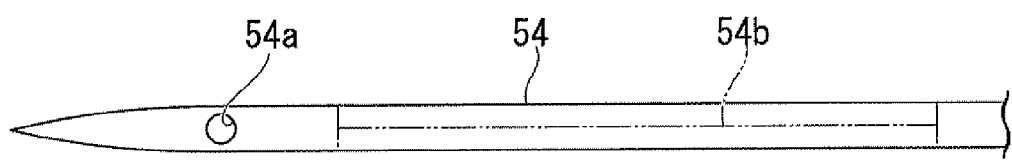
Figure 21C:
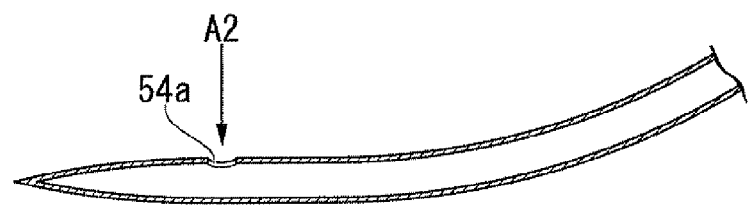

As shown in FIGS. 21A to 21C, the distal end of the needle tube 54 is sharp, and an opening 54a is provided in its side face. The direction to visualize this opening 54a from the front, i.e. the direction to visualize the largest area (indicated by arrow A2 in FIGS. 21A and 21C) is substantially parallel with the plane 54b that contains the long center axis of the needle tube 54. While this example has one opening, another opening can be provided in accordance with the desired dispersal range of the medicine (e.g. at a position 180 degrees opposite thereto), or a plurality of openings can provided along the longitudinal direction of the needle tube 54.

Figure 22A:
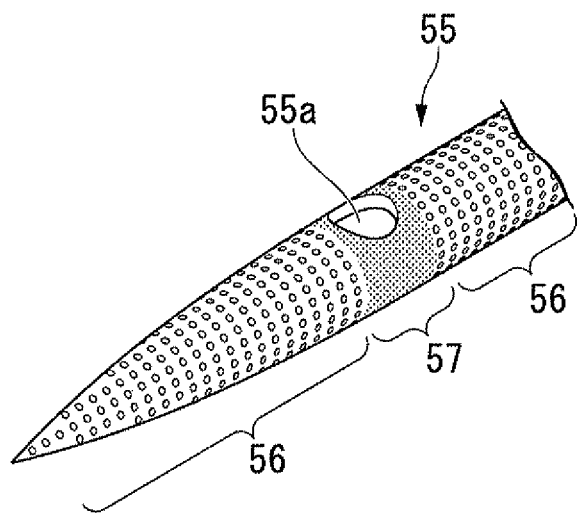
FIGS. 22A and 22B are examples of an ultrasonic reflection process performed to the needle tube.
Figure 22B:
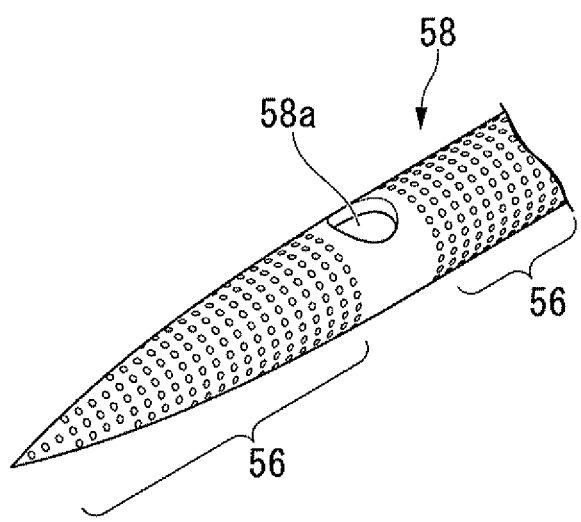

With a conventional ultrasonic puncture needle, ultrasonic reflection machining is sometimes used to enhance the visibility of the needle tube on the ultrasonic image. In ultrasonic reflection machining, a great many minute recesses such as dimples are formed in the needle tube surface, and the surface is made rougher. With regard to this ultrasonic reflection machining, the needle tube 54 is configured so that ultrasonic is reflected differently from near the opening 54a and from the distal-end side and proximal-end side of the opening 54a. FIGS. 22A and 22B are specific examples of such ultrasonic reflection.

In FIG. 22A, ultrasonic reflection machining 57 is performed around an opening 55a in a needle tube 55, and ultrasonic reflection machining 56 with a different ultrasonic reflectivity to the ultrasonic reflection machining 57 is performed at the front and rear of the opening 55a in the longitudinal direction. In FIG. 22B, machining is not performed to the surface around an opening 58a in a needle tube 58, and ultrasonic reflection machining 56 is performed at the front and rear of the opening 58a in the longitudinal direction, so that the ultrasonic reflection pattern is different.

By changing the reflectivity of ultrasonic near the opening and on the distal-end side and proximal-end side of the opening in this way, the brightness of the region near the opening on the ultrasonic image is different from the brightness of the distal-end side and proximal-end side, enabling the position of the opening to be confirmed clearly. Therefore, a substance can be supplied more accurately. The ultrasonic reflection machining formed at the front and rear of the opening in the longitudinal direction need only have a different ultrasonic reflectivity to the region around the opening, and is not limited to the pattern indicated by reference code 56.

In this embodiment, the mechanism for controlling the angular position of the needle tube around the axis is similar to that of the first embodiment, and will not be repetitiously explained.

(Fourth Embodiment)

An example where the configuration of the needle tube is different from that of the first to the third embodiments will be explained as a fourth embodiment. In this embodiment, the substance being delivered into the body can be a solid such as the implant 35, or it can be a gas or liquid such as the medicine 53. Other than the configuration of the needle tube, the ultrasonic puncture needle in this embodiment has the same configuration as the first embodiment when delivering a solid, and has the same configuration as the second embodiment when delivering a gas or liquid such as the medicine 53. Therefore, only points of difference will be described.

Figure 23:
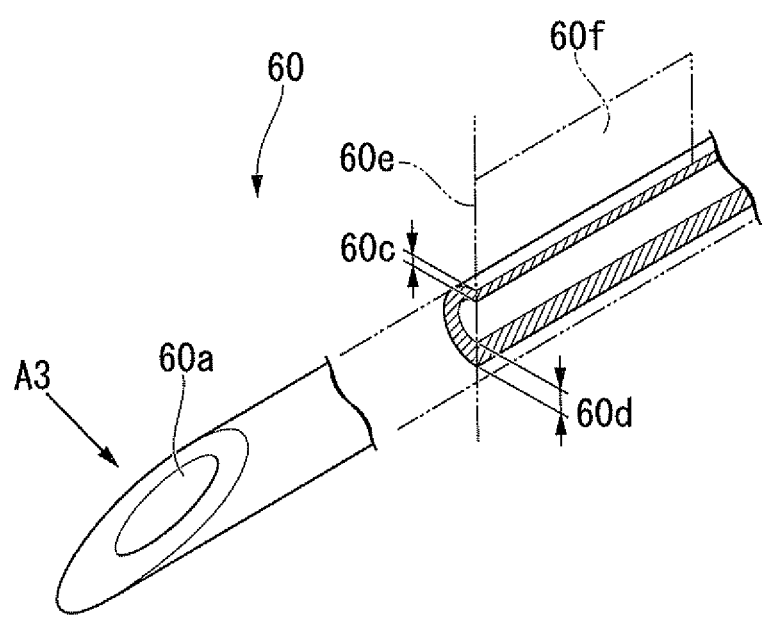
FIG. 23 is a view of the distal-end side of a needle tube of an ultrasonic puncture needle according to a fourth embodiment of the present invention.

The outer diameter of needle tube 60 shown in FIG. 23 is eccentric to the center of the inner cavity, and an opening 60a is formed at the distal end. The direction for visualizing the largest area of the opening 60a (indicated by arrow A3 in FIG. 23) is substantially parallel with a longitudinal cross-sectional plane 60f that contains a line 60e connecting the thinnest part 60c and the thickest part 60d of the needle tube. In a natural state where no external force is acting on it, the needle tube 60 maintains a linear shape (including substantially linear).

Figure 24A:
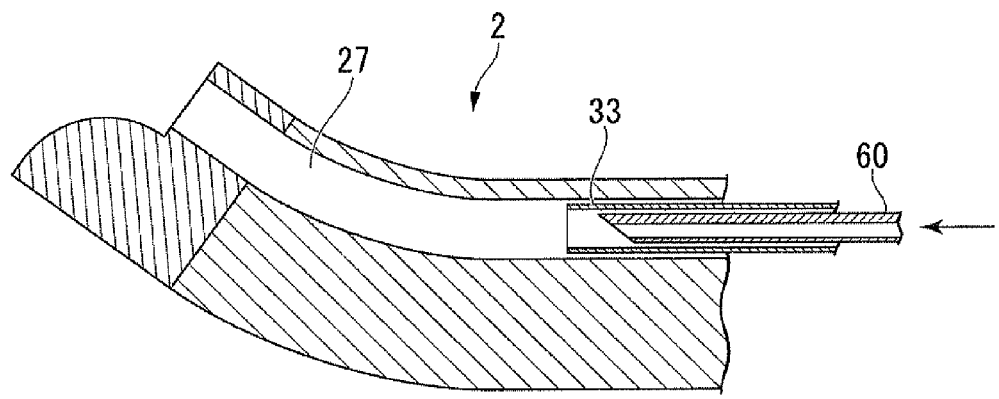
FIGS. 24A and 24B are views of an operation of the ultrasonic puncture needle according to the fourth embodiment of the present invention in a curved ultrasonic endoscope.
Figure 24B:
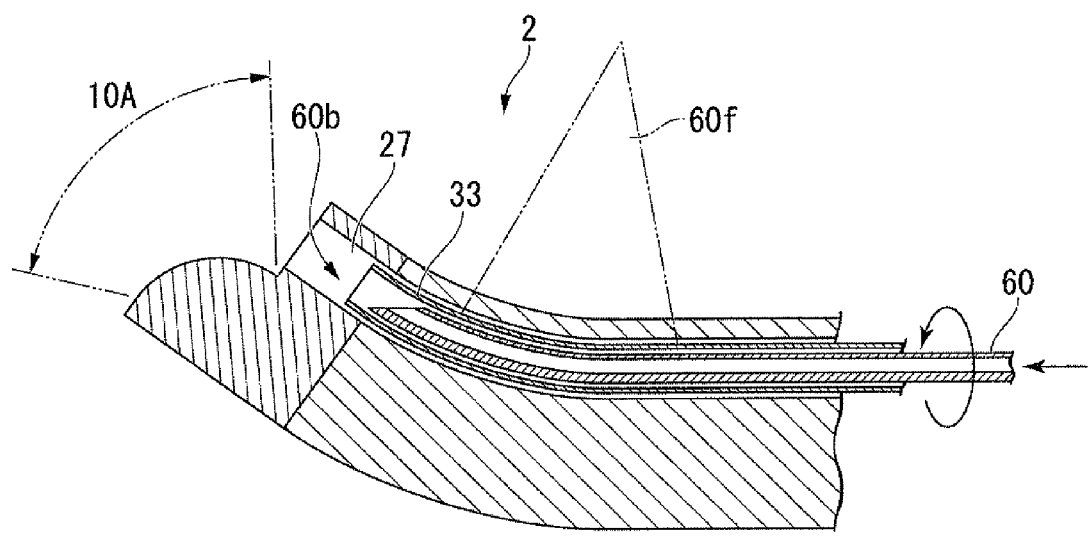

As shown in FIGS. 24A and 24B, when the insertion part of the ultrasonic puncture needle, containing the needle tube 60 with an outer diameter eccentric to its inner cavity, is passed into the insertion channel 27 of the curved ultrasonic endoscope 1, the needle tube 60 is made to rotate around the long axis so that the thinnest part of the needle tube 60 is on the inner side of the curve of the ultrasonic endoscope 1. As a result, the longitudinal cross-sectional plane 60f that contains the line 60 connecting the thinnest and thickest parts of the needle tube 60 becomes substantially the same as the ultrasonic scan plane 10A. Therefore, the direction A3 to visualize the largest area of the opening 60a becomes substantially parallel with the ultrasonic scan plane 10A. The substance that has been delivered can thus be favorably confirmed on the ultrasonic image.

(Fifth Embodiment)

An example where the configuration of the needle tube differs from those in the first to the fourth embodiments will be explained as a fifth embodiment. In this embodiment, the substance being delivered into the body can be a solid such as the implant 35, or it can be a gas or liquid such as the medicine 53. Other than the configuration of the distal end of the needle tube, the ultrasonic puncture needle in this embodiment has the same configuration as the first embodiment when delivering a solid, and has the same configuration as the second embodiment when delivering a gas or liquid such as the medicine 53. Therefore, only points of difference will be described.

Figure 25:
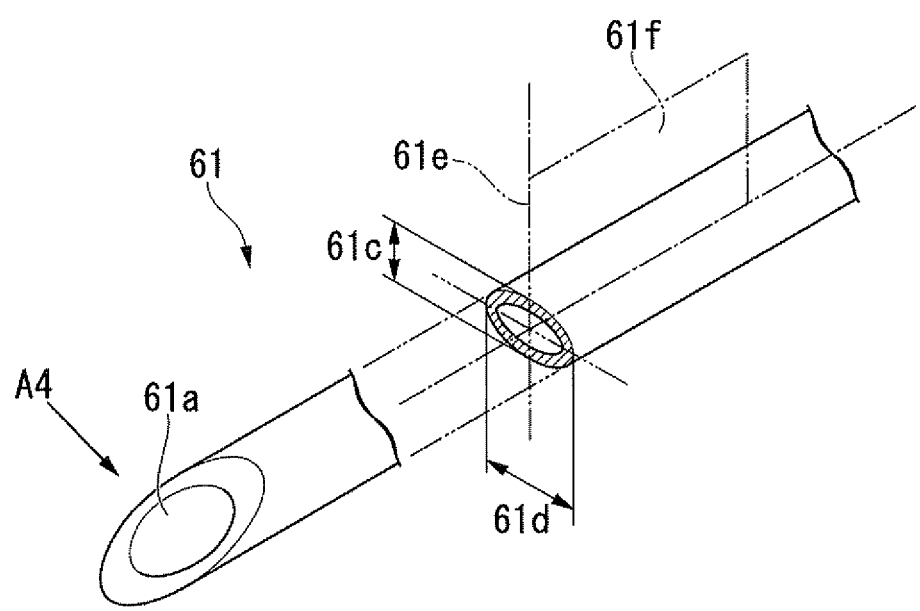
FIG. 25 is a view of the distal-end side of a needle tube of an ultrasonic puncture needle according to a fifth embodiment of the present invention.

A needle tube 61 shown in FIG. 25 has a flat cross-sectional shape, such as elliptical, oval, or rectangular, and the direction to visualize an opening 61a in the needle tube 61 (indicated by arrow A4 in FIG. 25) is substantially parallel with a longitudinal cross-sectional plane 61f that contains the short-diameter center axis 61e of the flat shape of the needle tube.

Figure 26A:
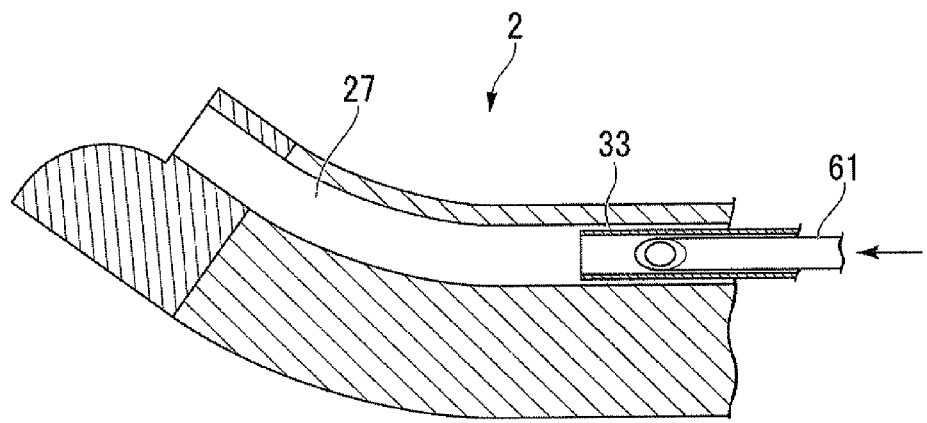
FIGS. 26A and 26B are views of an operation of the ultrasonic puncture needle according to the fifth embodiment of the present invention in a curved ultrasonic endoscope.
Figure 26B:
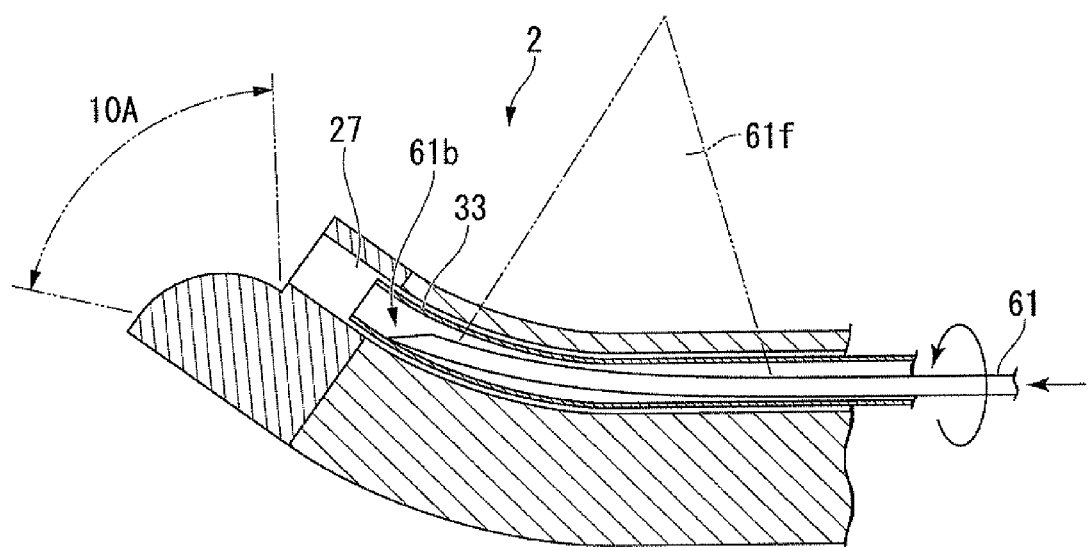

As shown in FIGS. 26A and 26B, when the insertion part of the ultrasonic puncture needle, containing the needle tube 61 with the flat cross-sectional shape, is passed into the insertion channel 27 of the curved ultrasonic endoscope 1, the needle tube 61 is made to rotate around the long axis in a direction such that the short-diameter side faces the center of the curve. As a result, the longitudinal cross-sectional plane 61f that contains the short-diameter center axis 61e of the needle tube becomes substantially parallel with the ultrasonic scan plane 10A. Therefore, the direction A4 to visualize the largest area of the opening 61a becomes substantially parallel with the ultrasonic scan plane 10A. Thus the substance that was delivered can be favorably confirmed on the ultrasonic image.

(Sixth Embodiment)

An example where the configuration of the needle tube differs from those in the first embodiment will be explained as a sixth embodiment. In this embodiment, the substance being delivered into the body is a solid such as the implant 35. Other than the configuration of the distal end of the needle tube, this embodiment has the same configuration as the first embodiment. Therefore, only points of difference will be described.

Figure 27:
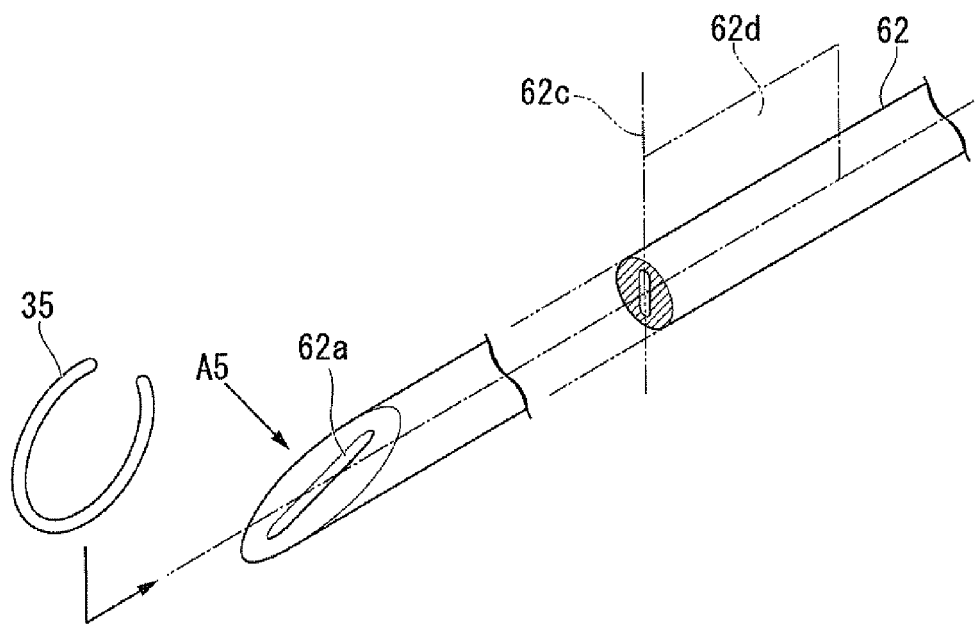
FIG. 27 is a view of the distal-end side of a needle tube of an ultrasonic puncture needle according to the sixth embodiment of the present invention.

The inner cavity of a needle tube 62 shown in FIG. 27 has a flat cross-sectional shape, such as elliptical, oval, or rectangular, and the direction to visualize an opening 62a in the needle tube (indicated by arrow A5 in FIG. 27) is substantially parallel with a longitudinal cross-sectional plane 62d that contains the long-diameter direction 62c of the flat shape.

The implant 35 is stored in the needle tube 62. Since the implant 35 attempts to return to its original shape inside the needle tube 62, it is stored such that it stretches in the long-diameter direction in the inner cavity.

Figure 28:
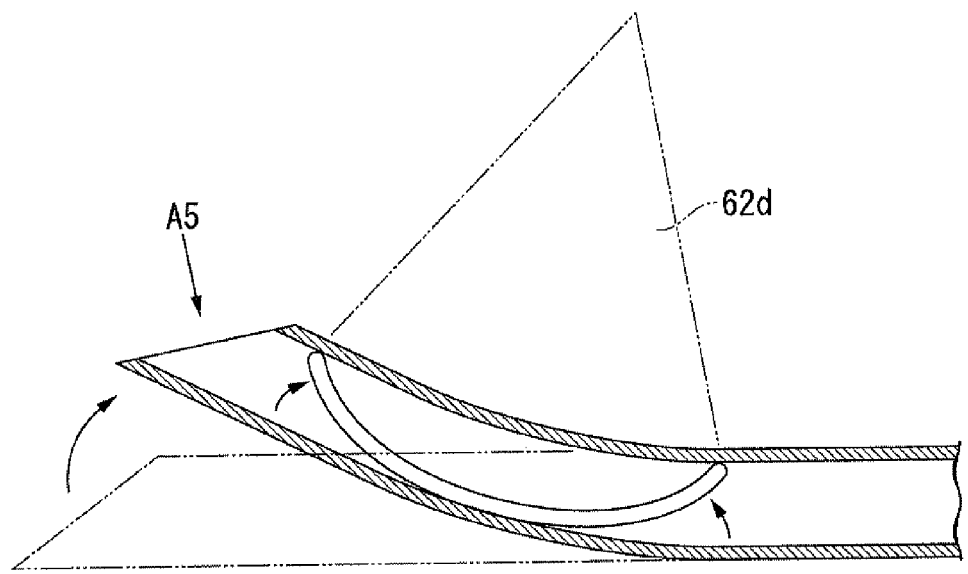
FIG. 28 is a view of a state where an implant has been stored in the needle tube according to the sixth embodiment of the present invention.

The needle tube 62 has a certain amount of flexibility, and the force of the implant 35 attempting to return to its original shape is strong enough to make the needle tube 62 curve. Consequently, as shown in FIG. 28, the section of the needle tube 62 which the implant 35 is stored in (i.e. the region near the distal end) curves in a smooth circular-arc shape in the longitudinal cross-sectional plane 62d. As a result, while the size of the circular-arc shape region of the needle tube 62 depends on the size of the implant 35, in external appearance it attains a shape broadly similar to that of the needle tube 34 shown in FIG. 12.

Thus in this embodiment, as in the first embodiment, the implant 35 can be favorably confirmed on the ultrasonic image.

As described above, according to embodiment of this invention, by matching the angular direction position of the needle tube opening part to the ultrasonic scan plane of the ultrasonic endoscope, it is possible to provide an ultrasonic puncture needle capable of accurately delivering a substance to a region of interest while favorably observing the delivery of the substance with an ultrasonic endoscope.

The invention is not limited to the embodiments described above, and can be modified in various ways without departing from the main points. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An ultrasonic puncture needle used in combination with an ultrasonic endoscope including a distal-end hard part, a bendable part which is connected to a proximal end of the distal-end hard part and which is bendable, and an operation part which performs bending operation of the bendable part, the ultrasonic puncture needle comprising:

a sheath that is inserted into an insertion channel of the ultrasonic endoscope so as to be capable of advancing and retreating;

a needle tube that has a predetermined outer diameter so as to be inserted into the sheath, and a sharp distal end configured to puncture a tissue in a body cavity; and a releasing mechanism that is fitted to a proximal-end side of the needle tube, and releases a substance filled therein from an opening of the needle tube to the outside, wherein the needle tube has an inner cavity which extends along a longitudinal axis of the needle tube and which centers on a position displaced from a center of the outer diameter, a thinnest part in which a thickness of a border of the opening, which is formed in a distal-end region of the needle tube so as to communicate with the inner cavity, is the thinnest, and a thickest part in which the thickness is the thickest, a direction of the opening of the needle tube is substantially parallel with a cross-ectional plane connecting the thinnest part and the thickest part, in a state in which the needle tube is disposed inside the bendable part, a periphery of the needle tube receives a force from an inner wall of the insertion channel while the bendable part is in a bent state by the operation part, and the needle tube is rotated around a longitudinal axis of the insertion channel by the force, such that the thinnest part is positioned on an inside of the bendable part and an axis line matching the direction of the opening in the needle tube protruding from the insertion channel becomes substantially parallel with an ultrasonic scanning face of the ultrasonic endoscope.

2. The ultrasonic puncture needle according to claim 1, wherein in a natural state, at least a region near the distal end of the needle tube is curved smoothly in a circular arc, and a direction to visualize a largest area of the opening of the needle tube is substantially parallel with a plane formed by a circular-arc shape of the needle tube.

3. The ultrasonic puncture needle according to claim 1, wherein an outer-diameter cross-sectional face of the needle tube has a flat shape, and a direction to visualize a largest area of the opening of the needle tube is substantially parallel with a short-diameter cross-sectional plane of the flat shape.

4. The ultrasonic puncture needle according to claim 1, wherein in a natural state, at least a region near the distal end of the needle tube is curved smoothly in a circular arc, and a most proximal-end side of the opening of the needle tube is in a plane formed by a circular-arc shape of the needle tube.

5. The ultrasonic puncture needle according to claim 1, wherein a most proximal-end side of the opening of the needle tube is in a cross-sectional plane connecting the thinnest part and the thickest part.

6. The ultrasonic puncture needle according to claim 1, wherein an outer-diameter cross-sectional face of the needle tube has a flat shape, and a most proximal-end side of the opening of the needle tube is in a short-diameter cross-sectional plane of the flat shape.

7. The ultrasonic puncture needle according to claim 1, wherein an inner cavity cross-sectional plane of the needle tube has a flat shape, and a direction to visualize a largest area of the opening is parallel with a longitudinal direction of the flat shape.

8. The ultrasonic puncture needle according to claim 1, wherein an ultrasonic reflection machining for obtaining a reflected echo is performed on a distal-end part surface of the needle tube, a pattern of the ultrasonic reflection machining around the opening being different from that in other regions.

9. The ultrasonic puncture needle according to claim 1, wherein the distal-end region covers the distal end.

10. The ultrasonic puncture needle according to claim 1, wherein the distal-end region covers a region near the distal end.

11. The ultrasonic puncture needle according to claim 1, wherein the substance includes gas.

12. The ultrasonic puncture needle according to claim 1, wherein the substance includes liquid.

13. The ultrasonic puncture needle according to claim 1, wherein the substance includes a solid.

14. The ultrasonic puncture needle according to claim 13, wherein the solid includes a slender elastic body.

* * * * *